(12) United States Patent
Liechti et al.

(10) Patent No.: US 11,717,517 B2
(45) Date of Patent: Aug. 8, 2023

(54) LSD DOSE IDENTIFICATION

(71) Applicant: Universitätsspital Basel, Basel (CH)

(72) Inventors: Matthias Emanuel Liechti, Oberwil (CH); Friederike Sophie Holze, Naters (CH)

(73) Assignee: Universitatsspital Basel, Basel (CH)

( * ) Notice: Subject to any disclaimer, the term of this patent is extended or adjusted under 35 U.S.C. 154(b) by 107 days.

(21) Appl. No.: 17/225,715

(22) Filed: Apr. 8, 2021

(65) Prior Publication Data

US 2021/0315884 A1    Oct. 14, 2021

Related U.S. Application Data

(60) Provisional application No. 63/050,780, filed on Jul. 11, 2020, provisional application No. 63/008,990, filed on Apr. 13, 2020.

(51) Int. Cl.

| | | |
|---|---|---|
| *A61K 31/48* | (2006.01) | |
| *A61K 31/4045* | (2006.01) | |
| *A61K 31/675* | (2006.01) | |
| *A61P 25/24* | (2006.01) | |
| *G01N 33/68* | (2006.01) | |
| *A61K 31/137* | (2006.01) | |

(52) U.S. Cl.
CPC .......... *A61K 31/48* (2013.01); *A61K 31/137* (2013.01); *A61K 31/4045* (2013.01); *A61K 31/675* (2013.01); *A61P 25/24* (2018.01); *G01N 33/6893* (2013.01); *G01N 2800/304* (2013.01); *G01N 2800/52* (2013.01)

(58) Field of Classification Search
CPC .. A61K 31/137; A61K 31/4045; A61K 31/48; A61K 31/675; A61P 25/24; G01N 2800/30; G01N 2800/304; G01N 2800/52; G01N 33/6893; G01N 33/6896
See application file for complete search history.

(56) References Cited

PUBLICATIONS

Anderson et al. (Harm Reduction Journal (2019) 16;43, pp. 1-10) (Year: 2019).*
Ross (Journal of Psychopharm (2019). pp. 1050-1051) (Year: 2019).*
(Continued)

*Primary Examiner* — Savitha M Rao
(74) *Attorney, Agent, or Firm* — Kohn & Associates PLLC

(57) ABSTRACT

A method of dosing and treating patients with a psychedelic, by administering a psychedelic at a dose of a microdose, minidose, psychedelic dose, good effect dose, ego-dissolution dose, or cardiovascular safe dose, and producing maximum positive subjective acute effects that are known to be associated with more positive long-term outcomes and minimizing negative acute effects. A method of determining a dose of a psychedelic for an individual, by administering a dose of a psychedelic to the individual of a microdose, minidose, psychedelic dose, good effect dose, ego-dissolution dose, or cardiovascular safe dose, determining positive acute effects and negative acute effects in the individual, and adjusting the dose to provide more positive acute effects than negative acute effects in the individual. Methods of treating psychiatric conditions or providing therapy. A method of defining therapeutic doses of a psychedelic in clinical trials. A method of monitoring individuals for depression after treatment with LSD.

31 Claims, 21 Drawing Sheets

(56) References Cited

PUBLICATIONS

Nichols et al.( Clinical Pharmacology and Therapeutics (2017) vol. 101, (2), pp. 209-219). (Year: 2017).*
Dos Santos et al. (Ther. Adv Psychopharmacology, 2016, vol. 693), 193-213). (Year: 2016).*
Karege et al. (Psychiatry Research 109 (2002) pp. 143-148). (Year: 2002).*
Akimoto H, Oshima S, Sugiyama T, Negishi A, Nemoto T, & Kobayashi D (2019). Changes in brain metabolites related to stress resilience: Metabolomic analysis of the hippocampus in a rat model of depression. Behav Brain Res 359: 342-352.
Barrett FS, Johnson MW, & Griffiths RR (2015). Validation of the revised Mystical Experience Questionnaire in experimental sessions with psilocybin. J Psychopharmacol 29: 1182-1190.
Barrett FS, Preller KH, Herdener M, Janata P, & Vollenweider FX (2018). Serotonin 2A Receptor Signaling Underlies LSD-induced Alteration of the Neural Response to Dynamic Changes in Music. Cereb Cortex 28: 3939-3950.
Bershad AK, Preller KH, Lee R, Keedy S, Wren-Jarvis J, Bremmer MP, & de Wit H (2020). Preliminary report on the effects of a low dose of LSD on resting-state amygdala functional connectivity. Biol Psychiatry Cogn Neurosci Neuroimaging 5: 461-467.
Bershad AK, Schepers ST, Bremmer MP, Lee R, & de Wit H (2019). Acute subjective and behavioral effects of microdoses of lysergic acid diethylamide in healthy human volunteers. Biol Psychiatry 86: 792-800.
Carhart-Harris RL, Kaelen M, Bolstridge M, Williams TM, Williams LT, Underwood R, Feilding A, & Nutt DJ (2016a). The paradoxical psychological effects of lysergic acid diethylamide (LSD). Psychol Med 46: 1379-1390.
Carhart-Harris RL, Kaelen M, Whalley MG, Bolstridge M, Feilding A, & Nutt DJ (2015). LSD enhances suggestibility in healthy volunteers. Psychopharmacology 232: 785-794.
Carhart-Harris RL, Muthukumaraswamy S, Roseman L, Kaelen M, Droog W, Murphy K, Tagliazucchi E, Schenberg EE, Nest T, Orban C, Leech R, Williams LT, Williams TM, Bolstridge M, Sessa B, McGonigle J, Sereno MI, Nichols D, Hellyer PJ, Hobden P, Evans J, Singh KD, Wise RG, Curran HV, Feilding A, & Nutt DJ (2016b). Neural correlates of the LSD experience revealed by multimodal neuroimaging. Proc Natl Acad Sci U S A 113: 4853-4858.
De Almeida RN, Galvao ACM, da Silva FS, Silva E, Palhano-Fontes F, Maia-de-Oliveira JP, de Araujo LB, Lobao-Soares B, & Galvao-Coelho NL (2019). Modulation of Serum Brain-Derived Neurotrophic Factor by a Single Dose of Ayahuasca: Observation From a Randomized Controlled Trial. Front Psychol 10: 1234.
Dittrich A (1998). The standardized psychometric assessment of altered states of consciousness (ASCs) in humans. Pharmacopsychiatry 31 (Suppl 2): 80-84.
Dolder PC, Schmid Y, Mueller F, Borgwardt S, & Liechti ME (2016). LSD acutely impairs fear recognition and enhances emotional empathy and sociality. Neuropsychopharmacology 41: 2638-2646.
Dolder PC, Schmid Y, Steuer AE, Kraemer T, Rentsch KM, Hammann F, & Liechti ME (2017). Pharmacokinetics and pharmacodynamics of lysergic acid diethylamide in healthy subjects. Clin Pharmacokinetics 56: 1219-1230.
Family N, Maillet EL, Williams LTJ, Krediet E, Carhart-Harris RL, Williams TM, Nichols CD, Goble DJ, & Raz S (2020). Safety, tolerability, pharmacokinetics, and pharmacodynamics of low dose lysergic acid diethylamide (LSD) in healthy older volunteers. Psychopharmacology 237: 841-853.
Garcia-Romeu A, Griffiths RR, & Johnson MW (2015). Psilocybin-occasioned mystical experiences in the treatment of tobacco addiction. Curr Drug Abuse Rev 7: 157-164.
Gasser P, Holstein D, Michel Y, Doblin R, Yazar-Klosinski B, Passie T, & Brenneisen R (2014). Safety and efficacy of Tysergic acid diethylamide-assisted psychotherapy for anxiety associated with life-threatening diseases. J Nerv Ment Dis 202: 513-520.

Gasser P, Kirchner K, & Passie T (2015). LSD-assisted psychotherapy for anxiety associated with a life-threatening disease: a qualitative study of acute and sustained subjective effects. J Psychopharmacol 29: 57-68.
Griffiths R, Richards W, Johnson M, McCann U, & Jesse R (2008). Mystical-type experiences occasioned by psilocybin mediate the attribution of personal meaning and spiritual significance 14 months later. J Psychopharmacol 22: 621-632.
Griffiths RR, Johnson MW, Carducci MA, Umbricht A, Richards WA, Richards BD, Cosimano MP, & Klinedinst MA (2016). Psilocybin produces substantial and sustained decreases in depression and anxiety in patients with lifethreatening cancer: a randomized double-blind trial. J Psychopharmacol 30: 1181-1197.
Griffiths RR, Richards WA, McCann U, & Jesse R (2006). Psilocybin can occasion mystical-type experiences having substantial and sustained personal meaning and spiritual significance. Psychopharmacology 187: 268-283; discussion 284-292.
Haile CN, Murrough JW, Iosifescu DV, Chang LC, Al Jurdi RK, Foulkes A, Iqbal S, Mahoney JJ, 3rd, De La Garza R, 2nd, Charney DS, Newton TF, & Mathew SJ (2014). Plasma brain derived neurotrophic factor (BDNF) and response to ketamine in treatment-resistant depression. Int J Neuropsychopharmacol 17: 331-336.
Hasler F, Grimberg U, Benz MA, Huber T, & Vollenweider FX (2004). Acute psychological and physiological effects of psilocybin in healthy humans: a double-blind, placebo-controlled dose-effect study. Psychopharmacology 172: 145-156.
Hintzen A, & Passie T (2010) The pharmacology of LSD: a critical review. Oxford University Press: Oxford.
Holze F, Duthaler U, Vizeli P, Muller F, Borgwardt S, & Liechti ME (2019). Pharmacokinetics and subjective effects of a novel oral LSD formulation in healthy subjects. Br J Clin Pharmacol 85: 1474-1483.
Holze F, Vizeli P, Ley L, Muller F, Dolder P, Stocker M, Duthaler U, Varghese N, Eckert A, Borgwardt S, & Liechti ME (2021). Acute dose-dependent effects of lysergic acid diethylamide in a double-blind placebo-controlled study in healthy subjects. Neuropsychopharmacology 46: 537-544.
Hutten N, Mason NL, Dolder PC, & Kuypers KPC (2019). Motives and side-effects of microdosing with psychedelics among users. Int J Neuropsychopharmacol 22: 426-434.
Hysek CM, Schmid Y, Simmler LD, Domes G, Heinrichs M, Eisenegger C, Preller KH, Quednow BB, & Liechti ME (2014). MDMA enhances emotional empathy and prosocial behavior. Soc Cogn Affect Neurosci 9: 1645-1652.
Hysek CM, Vollenweider FX, & Liechti ME (2010). Effects of a b-blockeron the cardiovascular response to MDMA (ecstasy). Emerg Med J 27: 586-589.
Janke W, & Debus G (1978) Die Eigenschaftswörterliste. Hogrefe: Göttingen.
Kaelen M, Barrett FS, Roseman L, Lorenz R, Family N, Bolstridge M, Curran HV, Feilding A, Nutt DJ, & Carhart-Harris RL (2015). LSD enhances the emotional response to music. Psychopharmacology 232: 3607-3614.
Kraehenmann R, Pokorny D, Aicher H, Preller KH, Pokorny T, Bosch OG, Seifritz E, & Vollenweider FX (2017a). LSD Increases Primary Process Thinking via Serotonin 2A Receptor Activation. Front Pharmacol 8: 814.
Kraehenmann R, Pokorny D, Vollenweider L, Preller KH, Pokorny T, Seifritz E, & Vollenweider FX (2017b). Dreamlike effects of LSD on waking imagery in humans depend on serotonin 2A receptor activation. Psychopharmacology 234: 2031-2046.
Krebs TS, & Johansen PO (2013). Over 30 million psychedelic users in the United States. F1000 Res 2: 98.
Kuypers KP, Ng L, Erritzoe D, Knudsen GM, Nichols CD, Nichols DE, Pani L, Soula A, & Nutt D (2019). Microdosing psychedelics: more questions than answers? An overview and suggestions for future research. J Psychopharmacol 33: 1039-1057.
Liechti ME (2017). Modern clinical research on LSD. Neuropsychopharmacology 42: 2114-2127.
Liechti ME, Dolder PC, & Schmid Y (2017). Alterations in conciousness and mystical-type experiences after acute LSD in humans. Psychopharmacology 234: 1499-1510.
Ly C, Greb AC, Cameron LP, Wong JM, Barragan EV, Wilson PC, Burbach KF, Soltanzadeh Zarandi S, Sood A, Paddy MR, Duim

(56) References Cited

PUBLICATIONS

WC, Dennis MY, McAllister AK, Ori-McKenney KM, Gray JA, & Olson DE (2018). Psychedelics promote structural and functional neural plasticity. Cell Rep 23: 3170-3182.

Mueller F, Dolder PC, Schmidt A, Liechti ME, & Borgwardt S (2018). Altered network hub connectivity after acute LSD administration. Neuroimage Clin 18: 694-701.

Mueller F, Lenz C, Dolder PC, Harder S, Schmid Y, Lang UE, Liechti ME, & Borgwardt S (2017a). Acute effects of LSD on amygdala activity during processing of fearful stimuli in healthy subjects. Transl Psychiatry 7: e1084.

Mueller F, Lenz C, Dolder PC, Lang UE, Schmidt A, Liechti ME, & Borgwardt S (2017b). Increased thalamic resting-state connectivity as a core driver of LSD-induced hallucinations. Acta Psychiatr Scand 136: 648-657.

Nichols DE (2016). Psychedelics. Pharmacological reviews 68: 264-355.

Nichols DE, & Grob CS (2018). Is LSD toxic? Forensic science international 284: 141-145.

Passie T, Halpern JH, Stichtenoth DO, Emrich HM, & Hintzen A (2008). The pharmacology of lysergic acid diethylamide: a review. CNS Neurosci Ther 14: 295-314.

Preller KH, Burt JB, Ji JL, Schleifer CH, Adkinson BD, Stampfli P, Seifritz E, Repovs G, Krystal JH, Murray JD, Vollenweider FX, & Anticevic A (2018). Changes in global and thalamic brain connectivity in LSD-induced altered states of consciousness are attributable to the 5-HT2A receptor. Elife 7: e35082.

Preller KH, Herdener M, Pokorny T, Planzer A, Kraehenmann R, Stampfli P, Liechti ME, Seifritz E, & Vollenweider FX (2017). The fabric of meaning and subjective effects in LSD-induced states depend on serotonin 2A receptor activation Curr Biol 27: 451-457.

Preller KH, Razi A, Zeidman P, Stampfli P, Friston KJ, & Vollenweider FX (2019). Effective connectivity changes in LSD-induced altered states of consciousness in humans. Proc Natl Acad Sci U S A 116: 2743-2748.

Roseman L, Nutt DJ, & Carhart-Harris RL (2017). Quality of acute psychedelic experience predicts therapeutic efficacy of psilocybin for treatment-resistant depression. Front Pharmacol 8: 974.

Ross S, Bossis A, Guss J, Agin-Liebes G, Malone T, Cohen B, Mennenga SE, Belser A, Kalliontzi K, Babb J, Su Z, Corby P, & Schmidt BL (2016). Rapid and sustained symptom reduction following psilocybin treatment for anxiety and depression in patients with life-threatening cancer: a randomized controlled trial. J Psychopharmacol 30: 1165-1180.

Schmid Y, Enzler F, Gasser P, Grouzmann E, Preller KH, Vollenweider FX, Brenneisen R, Mueller F, Borgwardt S, & Liechti ME (2015). Acute effects of lysergic acid diethylamide in healthy subjects. Biol Psychiatry 78: 544-553.

Schmid Y, & Liechti ME (2018). Long-lasting subjective effects of LSD in normal subjects. Psychopharmacology 235: 535-545.

Schmidt A, Mueller F, Lenz C, Dolder PC, Schmid Y, Zanchi D, Liechti ME, & Borgwardt S (2017). Acute LSD effects on response inhibition neuronal networks. Psychol Med 48: 1464-1473.

Steuer AE, Poetzsch M, Stock L, Eisenbeiss L, Schmid Y, Liechti ME, & Kraemer T (2017). Development and validation of an ultra-fast and sensitive microflow liquid chromatography-tandem mass spectrometry (MFLC-MS/MS) method for quantification of LSD and its metabolites in plasma and application to a controlled LSD administration study in humans. Drug Test Anal 9: 788-797.

Studerus E, Gamma A, Kometer M, & Vollenweider FX (2012). Prediction of psilocybin response in healthy volunteers. PLoS One 7: e30800.

Studerus E, Gamma A, & Vollenweider FX (2010). Psychometric evaluation of the altered states of consciousness rating scale (OAV). PLoS One 5: e12412.

Tagliazucchi E, Roseman L, Kaelen M, Orban C, Muthukumaraswamy SD, Murphy K, Laufs H, Leech R, McGonigle J, Crossley N, Bullmore E, Williams T, Bolstridge M, Feilding A, Nutt DJ, & Carhart-Harris R (2016). Increased global functional connectivity correlates with LSD-induced ego dissolution. Curr Biol 26: 1043-1050.

Yanakieva S, Polychroni N, Family N, Williams LTJ, Luke DP, & Terhune DB (2019). The effects of microdose LSD on time perception: a randomised, double-blind, placebo-controlled trial. Psychopharmacology 236: 1159-1170.

Zerssen DV (1976) Die Beschwerden-Liste. Münchener Informationssystem. Psychis: München.

\* cited by examiner

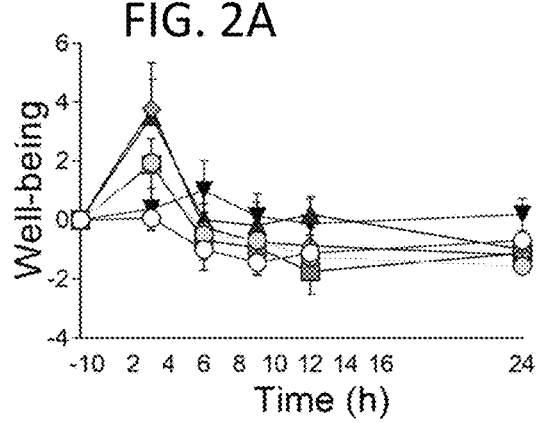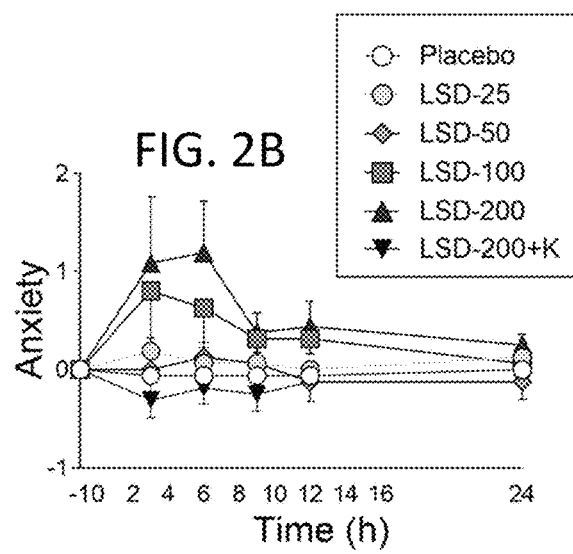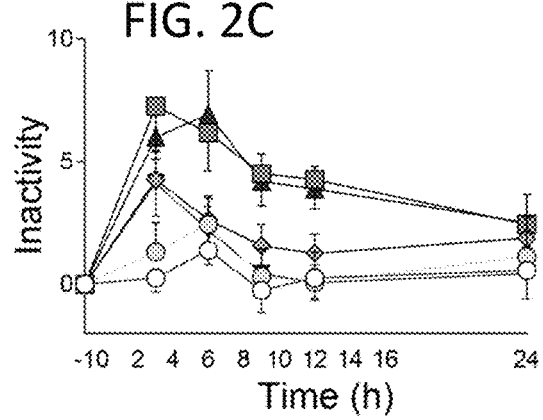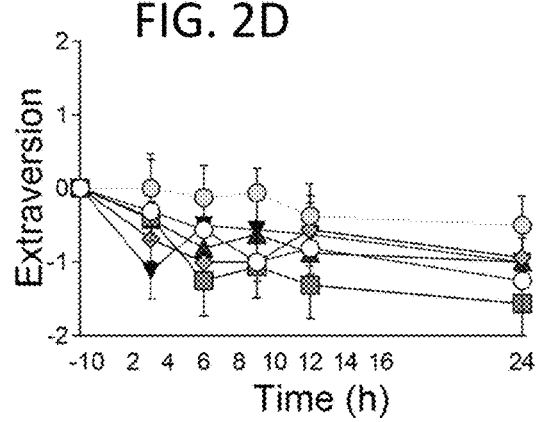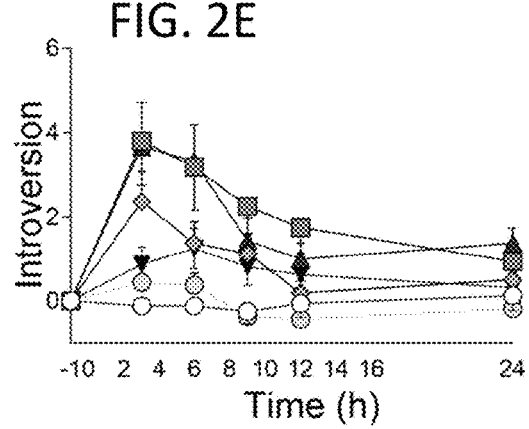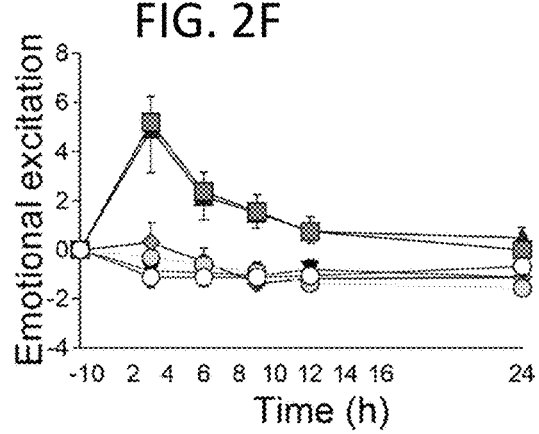

FIG. 3

Mean values and statistics for the acute effects of LSD alone, LSD + ketanserin, and placebo.

|  |  | Placebo (mean ± SEM) | LSD 25 μg (mean ± SEM) | LSD 50 μg (mean ± SEM) | LSD 100 μg (mean ± SEM) | LSD 200 μg (mean ± SEM) | LSD 200 μg + Ketanserin (mean ± SEM) | $F_{5,75}$ | P= |
|---|---|---|---|---|---|---|---|---|---|
| Subjective effects | | | | | | | | | |
| Visual Analoge Scale (VAS, %max) | | | | | | | | | |
| Any drug effect | $\Delta E_{max}$ | 0.9 ± 0.6 | 20 ± 3.8 | 57 ± 5.5 | 86 ± 5.7 | 83 ± 6.7 | 22 ± 4.9 | 72.9 | <0.001 |
|  | AUEC | 0.6 ± 0.4 | 58 ± 12 | 205 ± 32 | 431 ± 51 | 508 ± 82 | 133 ± 33 | 31.2 | <0.001 |
| Good drug effect | $\Delta E_{max}$ | 1.1 ± 0.8 | 32 ± 6.8 | 59 ± 6.7 | 81 ± 6.9 | 82 ± 6.6 | 22 ± 6.8 | 43.3 | <0.001 |
| Bad drug effect | $\Delta E_{max}$ | 0.1 ± 0.1 | 1.6 ± 0.8 | 1.5 ± 0.4 | 17 ± 5.9 | 28 ± 8.7 | 1.6 ± 0.6 | 8.82 | <0.001 |
| Drug liking | $\Delta E_{max}$ | 0.8 ± 0.5 | 32 ± 7.5 | 60 ± 6.7 | 79 ± 8.1 | 76 ± 7.8 | 26 ± 7.2 | 29.5 | <0.001 |
| Stimulated | $\Delta E_{max}$ | 0.1 ± 0.1 | 9.3 ± 3.3 | 40 ± 6.4 | 57 ± 10 | 66 ± 8.5 | 8.0 ± 2.4 | 27.8 | <0.001 |
| Fear | $\Delta E_{max}$ | 0.0 ± 0.0 | 0.2 ± 0.1 | 1.2 ± 0.8 | 11 ± 6.7 | 15 ± 8.4 | 0.4 ± 0.3 | 2.85 | <0.05 |
| Ego dissolution | $\Delta E_{max}$ | 0.0 ± 0.0 | 1.5 ± 0.7 | 21 ± 6.7 | 51 ± 9.6 | 73 ± 7.5 | 4.9 ± 3.7 | 35.6 | <0.001 |
| Concentration | $\Delta E_{max}$ | 0.0 ± 0.0 | 0.3 ± 0.2 | 3.4 ± 2.1 | 11 ± 4.3 | 11 ± 4.6 | 1.8 ± 1.1 | 4.31 | <0.01 |
|  | $\Delta E_{min}$ | -0.8 ± 0.7 | -6.4 ± 2.1 | -22 ± 3.6 | -37 ± 4.8 | -44 ± 2.9 | -7.8 ± 2.1 | 50.9 | <0.001 |
| Sense of time | $\Delta E_{max}$ | 0.1 ± 0.1 | 0.2 ± 0.1 | 0.7 ± 0.6 | 3.8 ± 3.0 | 13 ± 5.0 | 1.9 ± 1.6 | 4.54 | <0.01 |
|  | $\Delta E_{min}$ | -0.1 ± 0.1 | -5.4 ± 2.2 | -25 ± 4.4 | -32 ± 4.5 | -41 ± 3.3 | -3.4 ± 1.8 | 43.0 | <0.001 |

|  | Pla - 25 μg | Pla - 50 μg | Pla - 100 μg | Pla - 200 μg | Pla - 200 μg +K | 25 μg - 50 μg | 25 μg - 100 μg | 25 μg - 200 μg | 25 μg - 200 μg +K | 50 μg - 100 μg | 50 μg - 200 μg | 50 μg - 200 μg +K | 100 μg - 200 μg | 100 μg - 200 μg +K | 200 μg - 200 μg +K |
|---|---|---|---|---|---|---|---|---|---|---|---|---|---|---|---|
| Subjective effects | | | | | | | | | | | | | | | |
| Visual Analoge Scale (VAS, %max) | | | | | | | | | | | | | | | |
| Any drug effect | * | *** | *** | *** | * | *** | *** | *** | NS | *** | *** | *** | NS | *** | *** |
| AUEC | NS | ** | *** | *** | NS | NS | *** | *** | NS | *** | *** | NS | NS | *** | *** |
| Good drug effect | *** | *** | *** | *** | * | ** | *** | *** | NS | * | * | *** | NS | *** | *** |
| Bad drug effect | NS | NS | * | *** | NS | NS | *** | NS | *** | NS | NS | NS | NS | *** |
| Drug liking | *** | *** | *** | *** | * | * | *** | *** | NS | NS | NS | *** | NS | *** | *** |
| Stimulated | NS | *** | *** | *** | NS | ** | *** | *** | NS | NS | * | *** | NS | *** | *** |
| Fear | NS | NS | NS | NS | NS | NS | NS | NS | NS | NS | NS | NS | NS | NS | NS |
| Ego dissolution | NS | * | *** | *** | NS | NS | *** | *** | NS | ** | *** | NS | * | *** | *** |
| Concentration | NS | NS | * | * | NS | NS | * | * | NS | NS | NS | NS | NS | NS | NS |
| $\Delta E_{max}$ | NS | *** | *** | *** | NS | *** | *** | *** | NS | ** | *** | ** | NS | *** | *** |
| Sense of time | NS | NS | NS | ** | NS | NS | NS | ** | NS | NS | ** | NS | NS | NS | * |
| $\Delta E_{max}$ | NS | *** | *** | *** | NS | *** | *** | *** | NS | NS | *** | *** | NS | *** | *** |

*P<0.05, P<0.01, *P<0.001; NS, not significant; $E_{max}$, maximal effect; $\Delta E_{max}$, maximal difference from baseline; $C_{max}$, maximal concentration

FIG. 3 con't

| | | Placebo (mean ± SEM) | LSD 25 μg (mean ± SEM) | LSD 50 μg (mean ± SEM) | LSD 100 μg (mean ± SEM) | LSD 200 μg (mean ± SEM) | LSD 200 μg + Ketanserin (mean ± SEM) | $F_{5,75}$ | P= |
|---|---|---|---|---|---|---|---|---|---|
| 5 Dimensions of Altered States of Consciousness (ASC) Scale | | | | | | | | | |
| Total ASC score | % score | 0.1 ± 0.0 | 2.2 ± 0.6 | 9.5 ± 1.8 | 23 ± 2.9 | 30 ± 3.2 | 4.5 ± 1.5 | 52.0 | <0.001 |
| Oceanic boundlessness | % score | 0.0 ± 0.0 | 2.9 ± 1.0 | 12 ± 2.8 | 28 ± 4.7 | 36 ± 5.1 | 4.1 ± 2.2 | 29.3 | <0.001 |
| Anxious ego-dissolution | % score | 0.0 ± 0.0 | 0.6 ± 0.3 | 3.3 ± 1.1 | 11 ± 2.6 | 21 ± 5.4 | 1.1 ± 0.4 | 14.0 | <0.001 |
| Visionary restructuralization | % score | 0.1 ± 0.0 | 3.1 ± 1.2 | 18 ± 4.1 | 43 ± 5.4 | 50 ± 4.7 | 7.4 ± 3.1 | 45.9 | <0.001 |
| Auditory alterations | % score | 0.0 ± 0.0 | 0.4 ± 0.2 | 2.6 ± 1.0 | 9.1 ± 3.2 | 13 ± 3.3 | 2.5 ± 1.7 | 8.39 | <0.001 |
| Reductions of vigilance | % score | 0.6 ± 0.2 | 4.5 ± 1.7 | 12 ± 2.3 | 24 ± 4.8 | 27 ± 4.7 | 10 ± 2.8 | 16.6 | <0.001 |
| Experience of unity | % score | 0.0 ± 0.0 | 1.1 ± 0.7 | 10 ± 3.3 | 26 ± 6.0 | 40 ± 7.5 | 3.5 ± 2.6 | 17.4 | <0.001 |
| Spiritual experience | % score | 0.0 ± 0.0 | 0.9 ± 0.9 | 4.9 ± 2.4 | 17 ± 4.5 | 18 ± 4.1 | 3.0 ± 1.8 | 10.9 | <0.001 |
| Blissful state | % score | 0.1 ± 0.1 | 5.6 ± 1.8 | 18 ± 5.3 | 34 ± 7.8 | 33 ± 5.5 | 5.5 ± 2.6 | 10.5 | <0.001 |
| Insightfulness | % score | 0.0 ± 0.0 | 3.4 ± 1.8 | 9.9 ± 3.4 | 30 ± 6.1 | 29 ± 5.6 | 2.2 ± 1.1 | 17.7 | <0.001 |
| Disembodiment | % score | 0.0 ± 0.0 | 0.1 ± 0.1 | 3.6 ± 1.5 | 16 ± 5.8 | 37 ± 6.9 | 1.0 ± 0.6 | 16.9 | <0.001 |
| Impaired control and cognition | % score | 0.1 ± 0.1 | 1.6 ± 0.8 | 6.6 ± 2.4 | 19 ± 3.5 | 27 ± 5.2 | 2.4 ± 1.0 | 23.3 | <0.001 |
| Anxiety | % score | 0.0 ± 0.0 | 0.0 ± 0.0 | 0.5 ± 0.3 | 6.1 ± 3.0 | 17 ± 7.7 | 0.4 ± 0.3 | 4.51 | <0.01 |
| Complex imagery | % score | 0.0 ± 0.0 | 4.3 ± 2.2 | 19 ± 6.6 | 53 ± 8.2 | 62 ± 8.1 | 8.8 ± 3.7 | 28.5 | <0.001 |
| Elementary imagery | % score | 0.4 ± 0.3 | 2.6 ± 1.2 | 25 ± 6.9 | 50 ± 5.9 | 68 ± 6.6 | 14 ± 6.8 | 26.8 | <0.001 |
| Audio-visual synesthesia | % score | 0.0 ± 0.0 | 3.1 ± 1.6 | 25 ± 6.8 | 58 ± 8.4 | 70 ± 7.6 | 12 ± 5.2 | 28.5 | <0.001 |
| Changed meaning of percepts | % score | 0.0 ± 0.0 | 1.3 ± 0.6 | 12 ± 3.5 | 26 ± 8.0 | 30 ± 5.5 | 2.6 ± 1.3 | 12.9 | <0.001 |

| | Pla - 25 μg | Pla - 50 μg | Pla - 100 μg | Pla - 200 μg | Pla - 200 μg +K | 25 μg - 50 μg | 25 μg - 100 μg | 25 μg - 200 μg | 25 μg - 200 μg+K | 50 μg - 100 μg | 50 μg - 200 μg | 50 μg - 200 μg+K | 100 μg - 200 μg | 100 μg - 200 μg+K | 200 μg - 200 μg+K |
|---|---|---|---|---|---|---|---|---|---|---|---|---|---|---|---|
| 5 Dimensions of Altered States of Consciousness (ASC) Scale | | | | | | | | | | | | | | | |
| Total ASC score | NS | ** | *** | *** | NS | * | *** | *** | NS | *** | *** | NS | NS | *** | *** |
| Oceanic boundlessness | NS | * | *** | *** | NS | NS | *** | *** | NS | *** | *** | NS | NS | *** | *** |
| Anxious ego-dissolution | NS | NS | ** | *** | NS | NS | * | *** | NS | NS | *** | NS | * | * | *** |
| Visionary restructuralization | NS | ** | *** | *** | NS | * | *** | *** | NS | *** | *** | NS | NS | *** | *** |
| Auditory alterations | NS | NS | ** | *** | NS | NS | * | *** | NS | NS | ** | NS | NS | NS | ** |
| Reductions of vigilance | NS | * | *** | *** | NS | NS | *** | *** | NS | * | ** | NS | NS | ** | *** |
| Experience of unity | NS | NS | *** | *** | NS | NS | *** | *** | NS | * | *** | NS | NS | ** | *** |
| Spiritual experience | NS | NS | *** | *** | NS | NS | *** | *** | NS | * | ** | NS | NS | ** | *** |
| Blissful state | NS | NS | *** | *** | NS | NS | *** | *** | NS | NS | NS | NS | NS | *** | *** |
| Insightfulness | NS | NS | *** | *** | NS | NS | *** | *** | NS | *** | ** | NS | NS | *** | *** |
| Disembodiment | NS | NS | * | *** | NS | NS | * | *** | NS | NS | *** | NS | ** | * | *** |
| Impaired control and cognition | NS | NS | *** | *** | NS | NS | *** | *** | NS | ** | *** | NS | NS | *** | *** |
| Anxiety | NS | NS | NS | ** | NS | NS | NS | ** | NS | NS | ** | NS | NS | NS | ** |
| Complex imagery | NS | NS | *** | *** | NS | NS | *** | *** | NS | *** | *** | NS | NS | *** | *** |
| Elementary imagery | NS | * | *** | *** | NS | * | *** | *** | NS | * | *** | NS | NS | *** | *** |
| Audio-visual synesthesia | NS | * | *** | *** | NS | NS | *** | *** | NS | ** | *** | NS | NS | *** | *** |
| Changed meaning of percepts | NS | NS | *** | *** | NS | NS | *** | *** | NS | NS | * | NS | NS | *** | *** |

*P<0.05, P<0.01, *P<0.001; NS, not significant; $E_{max}$, maximal effect; $\Delta E_{max}$, maximal difference from baseline; $C_{max}$, maximal concentration

FIG. 3 con't

| | | Placebo (mean ± SEM) | LSD 25 µg (mean ± SEM) | LSD 50 µg (mean ± SEM) | LSD 100 µg (mean ± SEM) | LSD 200 µg (mean ± SEM) | LSD 200 µg + Ketanserin (mean ± SEM) | $F_{5,75}$ | $P=$ |
|---|---|---|---|---|---|---|---|---|---|
| Mystical Effects Questionnaire (MEQ43) | | | | | | | | | |
| Internal unity | % score | 0.0 ± 0.0 | 3.8 ± 1.6 | 14 ± 4.2 | 28 ± 6.3 | 38 ± 6.7 | 7.5 ± 3.7 | 16.3 | <0.001 |
| External unity | % score | 0.0 ± 0.0 | 3.3 ± 1.9 | 12.7 ± 3.7 | 26 ± 5.2 | 33 ± 5.3 | 9.8 ± 4.0 | 18.4 | <0.001 |
| Sacredness | % score | 0.0 ± 0.0 | 6.3 ± 2.4 | 19.1 ± 4.7 | 30 ± 6.5 | 34 ± 6.4 | 11 ± 4.8 | 12.1 | <0.001 |
| Noetic quality | % score | 1.3 ± 1.3 | 8.1 ± 3.7 | 15 ± 3.6 | 35 ± 6.6 | 27 ± 5.3 | 6.6 ± 3.2 | 16.4 | <0.001 |
| Deeply felt positive mood | % score | 0.0 ± 0.0 | 16 ± 4.1 | 30 ± 5.7 | 39 ± 5.9 | 44 ± 6.4 | 16 ± 5.6 | 16.1 | <0.001 |
| Transcendence of time/space | % score | 0.0 ± 0.0 | 6.3 ± 2.0 | 25 ± 5.0 | 46 ± 6.5 | 61 ± 7.0 | 11 ± 4.4 | 37.0 | <0.001 |
| Ineffability | % score | 0.0 ± 0.0 | 9.5 ± 4.1 | 32 ± 5.7 | 52 ± 4.9 | 61 ± 5.2 | 15 ± 5.7 | 40.3 | <0.001 |
| Mystical Effects Questionnaire (MEQ30) | | | | | | | | | |
| Mystical | % score | 0.3 ± 0.3 | 4.4 ± 2.0 | 14.8 ± 4.2 | 28 ± 6.4 | 32 ± 5.7 | 8.1 ± 3.8 | 14.4 | <0.001 |
| Positive mood | % score | 0.0 ± 0.0 | 18 ± 4.0 | 31 ± 5.2 | 42 ± 5.5 | 45 ± 6.4 | 17 ± 5.9 | 18.8 | <0.001 |
| Transcendence of time/space | % score | 0.0 ± 0.0 | 7.3 ± 2.2 | 26 ± 4.9 | 47 ± 6.0 | 61 ± 6.9 | 11 ± 4.3 | 39.9 | <0.001 |
| Ineffability | % score | 0.0 ± 0.0 | 13 ± 5.3 | 45 ± 7.1 | 71 ± 5.8 | 78 ± 6.0 | 19 ± 6.7 | 39.6 | <0.001 |
| MEQ30 total score | % score | 0.2 ± 0.2 | 8.5 ± 2.4 | 23 ± 4.4 | 39 ± 5.3 | 45 ± 5.4 | 12 ± 4.4 | 30.5 | <0.001 |
| Nadir | % score | 0.0 ± 0.0 | 1.4 ± 0.6 | 7.6 ± 2.5 | 14 ± 3.6 | 26 ± 6.8 | 4.3 ± 1.6 | 11.8 | <0.001 |
| Aesthetic Experience | % score | 0.5 ± 0.3 | 8.5 ± 2.78 | 28 ± 5.2 | 46 ± 5.8 | 48 ± 5.7 | 17 ± 4.2 | 27.4 | <0.001 |

| | Pla - 25 µg | Pla - 50 µg | Pla - 100 µg | Pla - 200 µg | Pla - 200 µg +K | 25 µg - 50 µg | 25 µg - 100 µg | 25 µg - 200 µg | 25 µg - 200 µg+K | 50 µg - 100 µg | 50 µg - 200 µg | 50 µg - 200 µg+K | 100 µg - 200 µg | 100 µg - 200 µg+K | 200 µg - 200 µg+K |
|---|---|---|---|---|---|---|---|---|---|---|---|---|---|---|---|
| Mystical Effects Questionnaire (MEQ43) | | | | | | | | | | | | | | | |
| Internal unity | NS | NS | *** | *** | NS | NS | *** | *** | NS | NS | *** | NS | NS | ** | *** |
| External unity | NS | * | *** | *** | NS | NS | *** | *** | NS | * | *** | NS | NS | ** | *** |
| Sacredness | NS | ** | *** | *** | NS | NS | *** | *** | NS | NS | NS | NS | NS | * | ** |
| Noetic quality | NS | * | *** | *** | NS | NS | *** | ** | NS | *** | NS | NS | NS | *** | *** |
| Deeply felt positive mood | NS | *** | *** | *** | NS | NS | ** | *** | NS | NS | NS | NS | NS | ** | *** |
| Transcendence of time/space | NS | *** | *** | *** | NS | * | *** | *** | NS | ** | *** | NS | NS | *** | *** |
| Ineffability | NS | *** | *** | *** | NS | ** | *** | *** | NS | ** | *** | * | NS | *** | *** |
| Mystical Effects Questionnaire (MEQ30) | | | | | | | | | | | | | | | |
| Mystical | NS | * | *** | *** | NS | NS | *** | *** | NS | NS | ** | NS | NS | ** | *** |
| Positive mood | * | *** | *** | *** | * | NS | *** | *** | NS | NS | NS | NS | NS | *** | *** |
| Transcendence of time/space | NS | *** | *** | *** | NS | ** | *** | *** | NS | ** | *** | NS | NS | *** | *** |
| Ineffability | NS | *** | *** | *** | NS | *** | *** | *** | NS | ** | *** | ** | NS | *** | *** |
| MEQ30 total score | NS | *** | *** | *** | NS | * | *** | *** | NS | * | *** | NS | NS | *** | *** |
| Nadir | NS | NS | ** | *** | NS | NS | * | *** | NS | NS | *** | NS | * | NS | *** |
| Aesthetic Experience | NS | *** | *** | *** | * | ** | *** | *** | NS | * | ** | NS | NS | *** | *** |

*P<0.05, P<0.01, *P<0.001; NS, not significant; $E_{max}$, maximal effect; $\Delta E_{max}$, maximal difference from baseline; $C_{max}$, maximal concentration

FIG. 3 con't

| | | Placebo (mean ± SEM) | LSD 25 µg (mean ± SEM) | LSD 50 µg (mean ± SEM) | LSD 100 µg (mean ± SEM) | LSD 200 µg (mean ± SEM) | LSD 200 µg + Ketanserin (mean ± SEM) | $F_{5,75}$ | $P=$ |
|---|---|---|---|---|---|---|---|---|---|
| Adjective Mood Rating Scale (AMRS score) | | | | | | | | | |
| Well-being | $\Delta E_{max}$ | 0.5 ± 0.3 | 2.6 ± 0.8 | 4.1 ± 1.0 | 3.1 ± 1.2 | 4.0 ± 1.3 | 2.3 ± 0.8 | 2.41 | <0.05 |
| Anxiety | $\Delta E_{max}$ | 0.0 ± 0.1 | 0.3 ± 0.1 | 0.2 ± 0.2 | 1.0 ± 0.5 | 1.8 ± 0.7 | 0.2 ± 0.2 | 4.07 | <0.01 |
| Inactivity | $\Delta E_{max}$ | 2.9 ± 0.8 | 4.3 ± 1.1 | 6.4 ± 1.0 | 9.4 ± 2.0 | 9.6 ± 1.6 | 5.4 ± 1.3 | 6.27 | <0.001 |
| Extraversion | $\Delta E_{max}$ | 0.1 ± 0.2 | 0.6 ± 0.4 | 0.5 ± 0.4 | 0.5 ± 0.4 | 0.8 ± 0.5 | 0.2 ± 0.3 | 0.74 | NS |
| Introversion | $\Delta E_{max}$ | 0.6 ± 0.3 | 0.8 ± 0.4 | 3.0 ± 0.7 | 4.8 ± 1.1 | 4.3 ± 0.9 | 1.9 ± 0.6 | 11.6 | <0.001 |
| Emotional excitation | $\Delta E_{max}$ | -0.6 ± 0.3 | -0.2 ± 0.4 | 0.9 ± 0.8 | 5.9 ± 1.9 | 5.4 ± 1.2 | 0.1 ± 0.5 | 9.25 | <0.001 |
| Autonomic effects | | | | | | | | | |
| Systolic blood pressure (mmHg) | $E_{max}$ | 131 ± 3.5 | 133 ± 3.0 | 137 ± 3.2 | 139 ± 3.5 | 138 ± 2.4 | 133 ± 3.0 | 5.05 | <0.001 |
| | $E_{min}$ | 110 ± 2.7 | 113 ± 2.9 | 115 ± 2.3 | 113 ± 2.9 | 117 ± 2.2 | 109 ± 3.0 | 6.77 | <0.001 |
| Diastolic blood pressure (mmHg) | $E_{max}$ | 80 ± 2.1 | 83 ± 1.7 | 84 ± 1.9 | 85 ± 2.0 | 87 ± 2.0 | 83 ± 1.8 | 4.76 | <0.001 |
| | $E_{min}$ | 64 ± 1.7 | 65 ± 1.7 | 67 ± 1.7 | 66 ± 1.7 | 69 ± 1.5 | 63 ± 1.8 | 6.57 | <0.001 |
| Heart rate (beats/min) | $E_{max}$ | 75 ± 2.7 | 76 ± 2.8 | 79 ± 2.1 | 83 ± 3.3 | 86 ± 3.9 | 77 ± 3.3 | 9.59 | <0.001 |
| Body temperature (°C) | $E_{max}$ | 37.3 ± 0.1 | 37.3 ± 0.07 | 37.4 ± 0.08 | 37.5 ± 0.09 | 37.5 ± 0.1 | 37.3 ± 0.09 | 2.17 | NS |
| List of Complaints (LC score) | | | | | | | | | |
| Acute adverse effects | 0-12 h | 1.6 ± 0.8 | 4.0 ± 1.0 | 6.1 ± 1.4 | 12 ± 2.5 | 13.5 ± 3.3 | 4.6 ± 1.1 | 10.8 | <0.001 |
| Subacute adverse effects | 12-24 h | 0.3 ± 0.3 | 0.8 ± 0.3 | 2.2 ± 1.6 | 5.9 ± 2.3 | 4.5 ± 1.9 | 4.4 ± 1.9 | 3.69 | <0.01 |
| Adverse Effects | $E_{max}$ | 1.7 ± 0.8 | 4.0 ± 1.0 | 6.8 ± 1.8 | 13 ± 2.5 | 14 ± 3.3 | 6.2 ± 1.8 | 11.0 | <0.001 |
| BDNF (pg/mL) | $C_{max}$ | 2953 ± 484 | 3800 ± 617 | 3561 ± 464 | 3848 ± 723 | 5685 ± 693 | 4372 ± 880 | 2.61 | <0.05 |

| | Pla - 25 µg | Pla - 50 µg | Pla - 100 µg | Pla - 200 µg | Pla - 200 µg +K | 25 µg - 50 | 25 µg - 100 | 25 µg - 200 | 25 µg - 200 µg+K | 50 µg - 100 | 50 µg - 200 | 50 µg - 200 µg+K | 100 µg - 200 | 100 µg - 200 µg+K | 200 µg - 200 µg+K |
|---|---|---|---|---|---|---|---|---|---|---|---|---|---|---|---|
| Adjective Mood Rating Scale (AMRS score) | | | | | | | | | | | | | | | |
| Well-being | NS | * | NS | NS | NS | NS | NS | NS | NS | NS | NS | NS | NS | NS | NS |
| Anxiety | NS | NS | NS | ** | NS | NS | NS | * | NS | NS | * | NS | NS | NS | * |
| Inactivity | NS | NS | *** | *** | NS | NS | * | * | NS | NS | NS | NS | NS | NS | NS |
| Extraversion | NS | NS | NS | NS | NS | NS | NS | NS | NS | NS | NS | NS | NS | NS | NS |
| Introversion | NS | * | *** | *** | NS | * | *** | *** | NS | NS | NS | NS | NS | ** | * |
| Emotional excitation | NS | NS | *** | *** | NS | NS | *** | ** | NS | ** | * | NS | NS | ** | ** |
| Autonomic effects | | | | | | | | | | | | | | | |
| Systolic blood pressure (mmHg) | NS | * | ** | * | NS | NS | NS | NS | NS | NS | NS | NS | NS | NS | NS |
| $E_{min}$ | NS | NS | NS | ** | NS | NS | NS | NS | NS | NS | ** | NS | NS | *** |
| Diastolic blood pressure (mmHg) | NS | NS | * | *** | NS | NS | NS | NS | NS | NS | NS | NS | NS | NS | NS |
| $E_{min}$ | NS | NS | NS | ** | NS | NS | NS | * | NS | NS | ** | NS | * | *** |
| Heart rate (beats/min) | NS | NS | ** | *** | NS | NS | * | *** | NS | NS | ** | NS | NS | *** |
| Body temperature (°C) | NS | NS | NS | NS | NS | NS | NS | NS | NS | NS | NS | NS | NS | NS |
| List of Complaints (LC score) | | | | | | | | | | | | | | | |
| Acute adverse effects | NS | NS | *** | *** | NS | NS | ** | *** | NS | * | ** | NS | NS | ** | *** |
| Subacute adverse effects | NS | NS | * | NS | NS | NS | * | NS | NS | NS | NS | NS | NS | NS |
| Adverse Effects | NS | NS | *** | *** | NS | NS | *** | *** | NS | * | * | NS | NS | * | ** |
| BDNF (pg/mL) | NS | NS | NS | * | NS | NS | NS | NS | NS | NS | NS | NS | NS | NS | NS |

*P<0.05, P<0.01, *P<0.001; NS, not significant; $E_{max}$, maximal effect; $\Delta E_{max}$, maximal difference from baseline; $C_{max}$, maximal concentration

FIG. 7

Acute adverse drug effects

|  | LSD 25 µg | | | LSD 50 µg | | | LSD 100 µg | | |
|---|---|---|---|---|---|---|---|---|---|
|  | 0h | 0-12h | 12-24h | 0h | 0-12h | 12-24h | 0h | 0-12h | 12-24h |
| Tiredness | 4 | 4 | 7 | 7 | 6 | 7 | 5 | 7 | 8 |
| Headache | 1 | 6 | 4 | 1 | 5 | 4 | 0 | 10 | 9 |
| Lack of concentration | 0 | 7 | 1 | 0 | 6 | 1 | 0 | 11 | 5 |
| Lack of appetite | 0 | 3 | 0 | 0 | 3 | 0 | 0 | 8 | 3 |
| Dullness | 0 | 4 | 1 | 1 | 3 | 2 | 0 | 5 | 4 |
| Brooding | 0 | 2 | 0 | 0 | 3 | 1 | 0 | 7 | 6 |
| Dry mouth | 1 | 2 | 2 | 0 | 3 | 3 | 0 | 4 | 2 |
| Feeling of weakness | 0 | 3 | 0 | 0 | 3 | 2 | 0 | 7 | 3 |
| Uneasiness | 0 | 1 | 0 | 1 | 4 | 1 | 0 | 9 | 2 |
| Hypersensitivity to certain odours | 0 | 2 | 0 | 0 | 4 | 2 | 0 | 5 | 2 |
| Lack of energy | 1 | 3 | 0 | 0 | 2 | 1 | 0 | 6 | 3 |
| Abdominal pain | 0 | 3 | 0 | 0 | 4 | 1 | 0 | 4 | 1 |
| Obliviousness | 0 | 1 | 0 | 0 | 3 | 2 | 0 | 5 | 4 |
| Crying tendency | 0 | 1 | 0 | 0 | 1 | 1 | 0 | 5 | 4 |
| Nausea | 0 | 2 | 0 | 0 | 0 | 0 | 0 | 5 | 1 |
| Rapid exhaustibility | 0 | 0 | 0 | 0 | 2 | 1 | 0 | 6 | 2 |
| Dizziness | 0 | 3 | 0 | 0 | 1 | 1 | 0 | 5 | 2 |
| Excessive urge to urinate | 0 | 2 | 1 | 0 | 2 | 1 | 0 | 3 | 1 |
| Feel of pressure or fullness | 0 | 0 | 0 | 0 | 3 | 0 | 0 | 3 | 1 |
| Imbalance | 0 | 1 | 0 | 0 | 0 | 1 | 0 | 7 | 1 |

|  | LSD 200 µg | | | LSD 200 µg + Ketanserin | | | Placebo | | |
|---|---|---|---|---|---|---|---|---|---|
|  | 0h | 0-12h | 12-24h | 0h | 0-12h | 12-24h | 0h | 0-12h | 12-24h |
| Tiredness | 4 | 5 | 7 | 6 | 11 | 9 | 5 | 8 | 4 |
| Headache | 0 | 5 | 4 | 1 | 5 | 5 | 0 | 3 | 3 |
| Lack of concentration | 0 | 8 | 3 | 1 | 7 | 3 | 0 | 2 | 0 |
| Lack of appetite | 0 | 8 | 1 | 0 | 4 | 2 | 0 | 1 | 0 |
| Dullness | 0 | 4 | 3 | 1 | 2 | 3 | 0 | 1 | 1 |
| Brooding | 1 | 4 | 3 | 0 | 2 | 4 | 0 | 1 | 0 |
| Dry mouth | 0 | 4 | 2 | 0 | 3 | 3 | 0 | 3 | 1 |
| Feeling of weakness | 0 | 5 | 2 | 0 | 2 | 3 | 0 | 0 | 0 |
| Uneasiness | 0 | 5 | 2 | 0 | 2 | 4 | 0 | 0 | 0 |
| Hypersensitivity to certain odours | 0 | 6 | 2 | 0 | 3 | 2 | 0 | 1 | 0 |
| Lack of energy | 0 | 3 | 2 | 1 | 4 | 3 | 0 | 1 | 0 |
| Abdominal pain | 1 | 3 | 2 | 0 | 3 | 3 | 0 | 2 | 0 |
| Obliviousness | 0 | 5 | 2 | 0 | 0 | 2 | 0 | 0 | 0 |
| Crying tendency | 0 | 5 | 3 | 0 | 1 | 2 | 0 | 0 | 0 |
| Nausea | 0 | 5 | 3 | 0 | 3 | 1 | 0 | 2 | 1 |
| Rapid exhaustibility | 0 | 5 | 3 | 1 | 1 | 2 | 0 | 0 | 0 |
| Dizziness | 0 | 3 | 0 | 0 | 4 | 1 | 0 | 0 | 0 |
| Excessive urge to urinate | 0 | 2 | 2 | 0 | 4 | 1 | 0 | 0 | 1 |
| Feel of pressure or fullness | 0 | 5 | 2 | 0 | 2 | 3 | 0 | 1 | 0 |
| Imbalance | 0 | 6 | 1 | 0 | 2 | 1 | 0 | 0 | 0 |

Data indicate number of subjects reporting an effect among a total of 16 subjects.

FIG. 8

Pharmacokinetic parameters for differnt doses of LSD based on compartmental modeling

| | Dose (µg) | | $K_{01}$ (1/h) | $\lambda_z$ (1/h) | $V_z/F$ (L) | $C_{max}$ (ng/mL) |
|---|---|---|---|---|---|---|
| LSD | 25 | Geometric mean (95% CI) | 2.0 (1.3-3.2) | 0.19 (0.16-0.24) | 38 (30-47) | 0.49 (0.41-0.58) |
| | | Range | 0.40-15.1 | 0.06-0.35 | 15-102 | 0.20-0.71 |
| | 50 | Geometric mean (95% CI) | 2.1 (1.5-3.0) | 0.19 (0.16-0.23) | 35 (31-38) | 1.1 (0.99-1.2) |
| | | Range | 0.43-19.8 | 0.06-0.44 | 22-46 | 0.68-1.6 |
| | 100 | Geometric mean (95% CI) | 1.8 (1.4-2.4) | 0.18 (0.15-0.21) | 37 (33-42) | 2.0 (1.9-2.2) |
| | | Range | 0.7-4.5 | 0.06-0.24 | 22-51 | 1.7-2.9 |
| | 200 | Geometric mean (95% CI) | 1.6 (1.2-2.1) | 0.17 (0.14-0.20) | 39 (35-43) | 3.9 (3.5-4.3) |
| | | Range | 0.45-5.03 | 0.06-0.35 | 25-67 | 2.5-6.0 |
| | 200 + Ketanserin | Geometric mean (95% CI) | 2.3 (1.4-3.8) | 0.15 (0.13-0.18) | 36 (32-40) | 4.4 (4.0-4.8) |
| | | Range | 0.6-20.0 | 0.06-0.24 | 23-47 | 3.1-6.8 |

| | | | $t_{max}$ (h) | $t_{1/2}$ (h) | $AUC_\infty$ (ng·h/mL) | $CL/F$ (L/h) |
|---|---|---|---|---|---|---|
| | 25 | Geometric mean (95% CI) | 1.2 (0.9-1.7) | 3.6 (2.9-4.4) | 3.5 (2.7-4.5) | 7.2 (5.6-9.3) |
| | | Range | 0.29-2.7 | 2.0-12 | 1.1-12 | 2.0-22 |
| | 50 | Geometric mean (95% CI) | 1.2 (0.95-1.6) | 3.6 (3.0-4.2) | 7.4 (6.2-8.9) | 6.7 (5.6-8.0) |
| | | Range | 0.25-2.5 | 1.6-11 | 4.2-25 | 2.0-11.8 |
| | 100 | Geometric mean (95% CI) | 1.4 (1.2-1.7) | 3.9 (3.2-4.7) | 15 (12-18) | 6.6 (5.4-8.0) |
| | | Range | 0.74-2.5 | 2.9-12 | 11-47 | 2.1-9.4 |
| | 200 | Geometric mean (95% CI) | 1.5 (1.3-1.9) | 4.1 (3.4-4.9) | 31 (25-38) | 6.5 (5.3-8.0) |
| | | Range | 0.70-5.0 | 2.0-11 | 18-127 | 1.6-11 |
| | 200 + Ketanserin | Geometric mean (95% CI) | 1.2 (0.85-1.8) | 4.5 (3.8-5.3) | 36 (30-43) | 5.6 (4.6-6.8) |
| | | Range | 0.25-4.1 | 0.25-4.1 | 25-110 | 1.8-7.9 |

$AUC_\infty$, area under the plasma concentration-time curve from time zero to infinity; $CL/F$ apparent total clearance; $C_{max}$, estimated maximum plasma concentration; $t_{1/2}$, estimated plasma elimination half-life; $t_{max}$, estimated time to reach $C_{max}$, $k_{01}$, first-order absorption koefficient; $\lambda_z$, first order elimination coefficient; $V_z/F$ volume of distribution.

FIG. 10

Characteristics of the subjective response to different doses of LSD

| Effect | 25 µg | 50 µg | 100 µg |
|---|---|---|---|
| Time to onset (h) | 1.0 ± 0.4 (0.6 - 1.8) | 0.7 ± 0.2 (0.4 - 1.2) | 0.6 ± 0.2 (0.4 - 0.9) |
| Time to offset (h) | 7.7 ± 2.1 (5.0 - 12.6) | 8.1 ± 2.3 (4.9 - 13) | 8.9 ± 3.0 (5.8 - 18) |
| Time to maximal effect (h) | 2.8 ± 0.8 (1.8 - 4.9) | 2.4 ± 0.6 (1.6 - 3.3) | 2.6 ± 1.1 (1.3 - 6.5) |
| Effect duration (h) | 6.7 ± 2.0 (4.3 - 12) | 7.4 ± 2.3 (4.4 - 12) | 8.3 ± 2.9 (5.0 - 18) |
| Maximal effect (%) | 17 ± 11 (0 - 37) | 46 ± 21 (7 - 86) | 76 ± 21 (13 - 97) |
|  | 200 µg | 200 µg + K |  |
| Time to onset (h) | 0.4 ± 0.2 (0.1 - 0.9) | not determinable |  |
| Time to offset (h) | 11 ± 4.9 (6.3 - 22) | not determinable |  |
| Time to maximal effect (h) | 2.2 ± 0.9 (1.3 - 5.1) | not determinable |  |
| Effect duration (h) | 11 ± 5.0 (5.6 - 22) | not determinable |  |
| Maximal effect (%) | 76 ± 26 (7 - 98) | not determinable |  |

Parameters are for "any drug effects" as predicted by the PK-PD link model. The threshold to determine times to onset and offset was set individually at 10% of the individual maximal response. Values are mean ± SD (range). Parameters could not be determined for the LSD plus ketanserin treatement condition because the response was too small.

FIG. 11

Pharmacokinetic parameters for different doses of LSD based on non-compartmental analyses

| | Dose (μg) | | Cmax (ng/mL) | tmax (h) | t1/2 (h) |
|---|---|---|---|---|---|
| LSD | 25 | Geometric mean | 0.51 | 1.2 | 4.2 |
| | | (95% CI) | (0.43-0.60) | (0.9-1.6) | (3.5-4.9) |
| | | Range | 0.21-0.69) | 0.4-3 | 3.2-11 |
| | 50 | Geometric mean | 1.1 | 1.2 | 3.9 |
| | | (95% CI) | (1.0-1.2) | (0.93-1.5) | (3.5-4.5) |
| | | Range | 0.79-1.5 | 0.50-3.0 | 3.0-9.7 |
| | 100 | Geometric mean | 2.0 | 1.2 | 4.0 |
| | | (95% CI) | (1.8-2.2) | (0.89-1.7) | (3.5-4.6) |
| | | Range | 1.6-2.9 | 0.50-3.0 | 3.2-8.1 |
| | 200 | Geometric mean | 3.8 | 1.5 | 4.2 |
| | | (95% CI) | (3.4-4.3) | (1.1-2.0) | (3.8-4.8) |
| | | Range | 2.4-6.9 | 0.4-6.0 | 2.8-9.0 |
| | 200 + Ketanserin | Geometric mean | 4.3 | 1.4 | 4.4 |
| | | (95% CI) | (4.0-4.7) | (0.95-2.1) | (3.7-5.3) |
| | | Range | 3.4-6.3 | 0.50-4.0 | 3.1-13 |

| | | | AUC24 (ng·h/mL) | AUC∞ (ng·h/mL) | CL/F (L/h) | Vz/F (L) |
|---|---|---|---|---|---|---|
| | 25 | Geometric mean | 3.4 | 3.6 | 6.8 | 42 |
| | | (95% CI) | (2.7-4.3) | (2.8-4.7) | (5.3-8.9) | (34-52) |
| | | Range | 1.1-8.9 | 1.2-12.3 | 2.0-20 | 25-143 |
| | 50 | Geometric mean | 7.4 | 7.7 | 6.5 | 37 |
| | | (95% CI) | (6.3-8.6) | (6.4-9.2) | (5.4-7.7) | (33-41) |
| | | Range | 4.3-19 | 4.4-25 | 2.0-11 | 30-51 |
| | 100 | Geometric mean | 15 | 15 | 6.5 | 38 |
| | | (95% CI) | (13-17) | (13-18) | (5.4-7.8) | (33-43) |
| | | Range | 10-35 | 11-44 | 2.2-9.3 | 22-52 |
| | 200 | Geometric mean | 29 | 31 | 6.5 | 40 |
| | | (95% CI) | (24-35) | (25-38) | (5.2-8.0) | (36-45) |
| | | Range | 18-97 | 18-132 | 1.5-11 | 20-60 |
| | 200 + Ketanserin | Geometric mean | 34 | 35 | 5.6 | 36 |
| | | (95% CI) | (28-40) | (29-44) | (4.6-6.8) | (32-40) |
| | | Range | 25-81 | 26-12 | 1.7-7.8 | 23-50 |

AUC, area under the plasma concentration-time curv; AUC∞, AUC from time zero to infinity; AUC24, from time 0-24; CL/F apparent total clearance; Cmax, maximum observed plasma concentration; T1/2, plasma half-life; Tmax, time to reach Cmax; 95%CI, 95% confidence interval; Vz/F, apparent volume of distribution

FIG. 12

Pharmacokinetic parameters for different doses of O-H-LSD based on non-compartmental analyses

| | LSD Dose (μg) | | Cmax (ng/mL) | tmax (h) | t1/2 (h) |
|---|---|---|---|---|---|
| O-H-LSD | 25 | Geometric mean (95% CI) | 0.03 (0.02-0.04) | 5.0 (4.0-6.1) | 8.6 (7.2-10) |
| | | Range | 0.01-0.05 | 2.0-10 | 5.2-21 |
| | 50 | Geometric mean (95% CI) | 0.07 (0.06-0.07) | 4.8 (4.0-5.7) | 8.5 (7.4-9.8) |
| | | Range | 0.04-0.12 | 2.0-10 | 5.7-23 |
| | 100 | Geometric mean (95% CI) | 0.12 (0.10-0.14) | 5.0 (4.1-6.1) | 8.3 (7.1-9.6) |
| | | Range | 0.06-0.18 | 3.0-10 | 5.8-18 |
| | 200 | Geometric mean (95% CI) | 0.25 (0.21-0.28) | 5.1 (4.4-5.9) | 8.2 (6.9-9.8) |
| | | Range | 0.15-0.39 | 3.9-10 | 5.5-27 |
| | 200 + Ketanserin | Geometric mean (95% CI) | 0.24 (0.20-0.29) | 4.9 (4.4-5.5) | 8.6 (7.2-10) |
| | | Range | 0.15-0.38 | 4.0-6.0 | 6.0-22 |

| | | | AUC24 (ng·h/mL) | AUC∞ (ng·h/mL) |
|---|---|---|---|---|
| | 25 | Geometric mean (95% CI) | 0.39 (0.31-0.47) | 0.48 (0.39-0.59) |
| | | Range | 0.16-0.71 | 0.19-0.89 |
| | 50 | Geometric mean (95% CI) | 0.82 (0.72-0.92) | 1.0 (0.9-1.2) |
| | | Range | 0.51-1.3 | 0.7-1.7 |
| | 100 | Geometric mean (95% CI) | 1.6 (1.4-1.8) | 1.9 (1.7-2.2) |
| | | Range | 1.1-2.3 | 1.2-3.3 |
| | 200 | Geometric mean (95% CI) | 3.3 (2.9-3.7) | 4.0 (3.5-4.7) |
| | | Range | 2.1-5.4 | 2.6-7.1 |
| | 200 + Ketanserin | Geometric mean (95% CI) | 3.2 (2.8-3.7) | 4.0 (3.5-4.6) |
| | | Range | 2.0-5.0 | 2.4-5.9 |

AUC, area under the plasma concentration-time curv; AUC∞, AUC from time zero to infinity; AUC24, from time 0-24; CL/F apparent total clearance; Cmax, maximum observed plasma concentration; T1/2, plasma half-life; Tmax, time to reach Cmax; 95%CI, 95% confidence interval; Vz/F, apparent volume of distribution

FIG. 13

Pharmacodynamic parameter estimates for the LSD effect (PK-PD link model)

| Effect | Dose (μg) | $EC_{50}$ (ng/ml) | $E_{max}$ (%) | γ | $k_{eo}$ (1/h) |
|---|---|---|---|---|---|
| any drug effect | 25 | 0.77±0.5 | 70±36 | 4.2±1.0 | 1.3±1.1 |
| | 50 | 0.88±0.3 | 81±30 | 4.1±1.3 | 1.9±1.5 |
| | 100 | 1.1±0.3 | 90±23 | 4.7±0.7 | 2.1±1.4 |
| | 200 | 2.0±0.9 | 83±28 | 5.3±3.0 | 4.5±3.1 |
| good drug effect | 25 | 1.1±0.6 | 60±42 | 4.5±0.6 | 1.6±1.1 |
| | 50 | 0.93±0.4 | 80±29 | 4.1±1.3 | 1.9±1.5 |
| | 100 | 1.2±0.4 | 83±30 | 4.5±0.9 | 1.9±1.0 |
| | 200 | 2.0±1.2 | 75±30 | 4.1±1.2 | 3.1±1.7 |
| bad drug effect | 25 | 2.1±0.5 | 6.3±15 | 4.7±0.4 | 2.1±0.9 |
| | 50 | 1.9±0.6 | 8.0±16 | 4.0±1.6 | 2.5±1.4 |
| | 100 | 2.0±1.0 | 20±34 | 3.1±1.3 | 3.1±1.5 |
| | 200 | 2.7±1.2 | 41±43 | 4.0±1.4 | 3.4±1.6 |
| ego dissolution | 25 | 2.1±0.4 | 9.8±22 | 4.6±0.5 | 1.8±0.5 |
| | 50 | 1.6±0.7 | 45±45 | 4.7±0.6 | 1.8±1.0 |
| | 100 | 1.8±0.5 | 69±39 | 4.2±1.2 | 2.5±1.7 |
| | 200 | 2.5±1.2 | 77±30 | 4.3±0.9 | 3.0±1.7 |

$E_{max}$, maximal effect predicted by the PK-PD link model; EC50, predicted drug concentration at effect site producing a half-maximal effect; γ, sigmoid shape parameter; $k_{eo}$, first-order rate constant for the equilibration process between plasma concentration and effect site (PK-PD model link parameter); values are means±standard deviations.

FIG. 14

Drug dose identification after each session and after the study

|  | LSD 200 μg | | LSD 100 μg | | LSD 50 μg | |
|---|---|---|---|---|---|---|
|  | after Session | after Study | after Session | after Study | after Session | after Study |
| correctly identified | 56% | 63% | 44% | 69% | 50% | 63% |
| missclassified as LSD 200 μg |  |  | 44% | 19% | 0% | 6% |
| missclassified as LSD 100 μg | 38% | 31% |  |  | 25% | 0% |
| missclassified as LSD 50 μg | 0% | 6% | 13% | 6% |  |  |
| missclassified as LSD 25 μg | 6% | 0% | 0% | 6% | 19% | 6% |
| missclassified as LSD 200 μg + ketanserin | 0% | 0% | 0% | 0% | 6% | 13% |
| missclassified as placebo | 0% | 0% | 0% | 0% | 0% | 13% |

|  | LSD 25 μg | | LSD 200 μg + Ketanserin | | Placebo | |
|---|---|---|---|---|---|---|
|  | after Session | after Study | after Session | after Study | after Session | after Study |
| correctly identified | 56% | 63% | 56% | 75% | 81% | 69% |
| missclassified as LSD 200 μg | 0% | 0% | 0% | 0% | 0% | 6% |
| missclassified as LSD 100 μg | 0% | 0% | 0% | 0% | 0% | 6% |
| missclassified as LSD 50 μg | 31% | 13% | 19% | 6% | 0% | 6% |
| missclassified as LSD 25 μg |  |  | 19% | 13% | 13% | 13% |
| missclassified as LSD 200 μg + ketanserin | 6% | 6% |  |  | 6% | 0% |
| missclassified as placebo | 6% | 13% | 6% | 6% |  |  |

LSD DOSE IDENTIFICATION

BACKGROUND OF THE INVENTION

1. Technical Field

The present invention relates to compositions and methods for identifying dose ranges for lysergic acid diethylamide to produce specific subjective drug effects in treating medical conditions.

2. Background Art

Lysergic acid diethylamide (LSD) is a prototypical hallucinogen that has been widely used for recreational and personal purposes (Krebs & Johansen, 2013). Additionally, LSD is increasingly used in experimental research (Carhart-Harris et al., 2016b; Dolder et al., 2016; Liechti, 2017; Preller et al., 2017; Schmid et al., 2015) and for the treatment of psychiatric patients (Gasser et al., 2014; Gasser et al., 2015). However, correct dosing of LSD to induce specific responses is a problem.

Although LSD has widely been used recreationally, the doses needed to produce specific desired therapeutic effects cannot be ascertained from prior experiential use of LSD because the LSD has been produced illicitly and sold in units lacking analytical identity information and in non-defined amounts without clear dose uniformity and without information on the possible presence of other psychoactive compounds. Even though LSD has increasingly been used in research and researchers reported the doses used in their publications, proof of the doses actually administered was mostly lacking.

Knowing the exact doses that are used to produce drug effects is critical. Although the production and evaluation of exact dose units is not part of the present invention and has been addressed recently (Holze et al., 2019), this aspect is presented because it is a prerequisite of the present invention that defines doses producing specific effects and because the problem of dose determination is partly aggravated by the use of non-defined doses both in reports of illicit LSD use and in research using LSD.

The formulations of LSD mostly used in recent clinical research did not have long-term stability and the doses actually administered to humans were therefore likely lower or at least unclear in these studies (Barrett et al., 2018; Dolder et al., 2016; Kraehenmann et al., 2017a; Kraehenmann et al., 2017b; Preller et al., 2018; Preller et al., 2017; Preller et al., 2019; Schmid et al., 2015). Specifically, longer-term stability data beyond the full study duration were unavailable for the capsules that were used in several previous studies (Dolder et al., 2016; Dolder et al., 2017; Kraehenmann et al., 2017b; Liechti et al., 2017; Mueller et al., 2018; Mueller et al., 2017a; Mueller et al., 2017b; Preller et al., 2017; Schmid et al., 2015; Schmid & Liechti, 2018; Schmidt et al., 2017). Further, after administration of the 200 µg dose in the form of two 100 µg capsules, iso-LSD was detected in plasma (Steuer et al., 2017), indicating that this inactive decomposition product of LSD was possibly already present in the capsules at the time of their use (although possible formation in the plasma samples cannot be completely excluded). The plasma $AUC_{24}$ values of LSD and iso-LSD of 21 and 9.2 ng×h/ml (Steuer et al., 2017) indicate that an average of 30% of the LSD may have isomerized to inactive iso-LSD in the capsules. Thus, the actual administered doses of LSD may have been 70 and 140 µg LSD base rather than the indicated 100 and 200 µg, respectively. The $AUC_{\infty}$ values in the previous studies that used 100 and 200 µg doses were 61% and 76%, respectively, of the values that were expected based on confirmed 96 µg LSD doses used in a later study (Holze et al., 2019) and assuming similar bioavailability. Finally, analytical tests of four unused old LSD capsules that were performed years after study completion suggested a marked reduction of LSD content (remaining amount of LSD=22±7 µg), indicating a lack of longer-term stability of LSD in this form and that the actual LSD doses that were used were likely already lower than indicated during the studies. Notably, a decrease in content by 15% or even 25% in single capsules would still be compatible with content uniformity, which was documented during production of the capsules. In summary, based on the results of different quality-control measures, analytical findings (including pharmacokinetic data (Holze et al., 2019)), and the clinical effects of the different formulations (Dolder et al., 2017), it is likely that previous studies actually used approximately 60-70 (not 100) µg and 140-150 (not 200) µg of LSD base, corresponding to approximately 80 and 175 µg of LSD tartrate.

Another consideration is that doses of LSD that were reported in previous studies may not have been very precise or may not have reflected the actual exposure of LSD in the body. This is notable in recent studies that used intravenous dosing with 75 µg hydrophobic LSD base in saline because objective measures of exposure to LSD (i.e., plasma concentrations) were lacking, and the bioavailability of the solution is unknown (Carhart-Harris et al., 2016a; Carhart-Harris et al., 2015; Carhart-Harris et al., 2016b; Kaelen et al., 2015; Tagliazucchi et al., 2016). The clinical response to 75 µg of intravenous LSD was not significantly different from the oral 100 µg dose that was used in previous studies (Carhart-Harris et al., 2016a; Liechti, 2017; Liechti et al., 2017), indirectly indicating similar exposure that is comparable to an oral dose of 60-70 µg LSD base.

In the light of the above noted data, even scientifically published data on LSD doses previously used is not sufficiently correct to guide safe and efficacious dose selection for medical treatment.

In addition to knowing the precise LSD dose administered in a dose-finding study, different doses need to be administered within the same study and preferably to the same human subjects to validly make claims on dosing. For example, previous published studies reported on the effects of 100 and 200 µg doses of LSD (Dolder et al., 2016). However, this data on different doses of LSD was generated in different studies, in different populations, and does not represent a valid dose-response assessment. Additionally, only relatively high doses were tested in most studies (100 or 200 µg orally) and very low doses of LSD tartrate have been tested in a few other studies (6.5, 13 and 26 µg (Bershad et al., 2020; Bershad et al., 2019) or 5, 10 and 20 µg (Family et al., 2020; Yanakieva et al., 2019)) but data covering a larger dose range within a study is missing.

There remains a need for an analysis of dosing of LSD and methods of dosing LSD accurately in medical treatments.

SUMMARY OF THE INVENTION

The present invention provides for a method of dosing and treating patients with a psychedelic, by administering a psychedelic at a dose of a microdose, minidose, psychedelic dose, good effect dose, ego-dissolution dose, or cardiovascular safe dose, and producing maximum positive subjective acute effects that are known to be associated with more positive long-term outcomes and minimizing negative acute effects.

The present invention also provides for a method of determining a dose of a psychedelic for an individual, by administering a dose of a psychedelic to the individual of a microdose, minidose, psychedelic dose, good effect dose, ego-dissolution dose, or cardiovascular safe dose, determining positive acute effects and negative acute effects in the individual, and adjusting the dose to provide more positive acute effects than negative acute effects in the individual.

The present invention provides for a method of treating psychiatric conditions in an individual, by administering a microdose of 1-20 µg of a psychedelic (preferably LSD) to the individual and treating a psychiatric condition.

The present invention provides for a method of therapy, by administering a good effect dose of 30-100 µg of a psychedelic (preferably LSD) to an individual and inducing positive acute drug effects that are known be associated with more positive long-term responses in psychiatric patients.

The present invention also provides for a method of therapy, by administering a defined ego-dissolution dose of greater than 100 µg of a psychedelic (preferably LSD) to an individual and providing ego-dissolution.

The present invention provides for a method of defining therapeutic doses of a psychedelic in clinical trials, by administering a dose of a psychedelic to a healthy individual in a phase 1 study of a microdose, minidose, psychedelic dose, good effect dose, ego-dissolution dose, or cardiovascular safe dose, determining positive acute effects and negative acute effects in the individual, adjusting the dose to provide more positive acute effects than negative acute effects in the individual, and using the adjusted dose for a phase 2 or phase 3 study in patients.

The present invention also provides for a method of monitoring individuals for depression after treatment with LSD, by measuring levels of brain-derived neurotrophic factor (BDNF) in the individual before and after LSD treatment, and determining whether the individual responded to treatment if BDNF increased.

DESCRIPTION OF THE DRAWINGS

Other advantages of the present invention are readily appreciated as the same becomes better understood by reference to the following detailed description when considered in connection with the accompanying drawings wherein:

FIG. 2A is a graph of well-being versus time, FIG. 2B is a graph of anxiety versus time, FIG. 2C is a graph of inactivity versus time, FIG. 2D is a graph of extraversion versus time, FIG. 2E is a graph of introversion versus time, and FIG. 2F is a graph of emotional excitation over time;

FIG. 3 is a table of a comparison of the acute effects of LSD alone, LSD+ketanserin, and placebo;

FIG. 7 is a table of acute adverse drug effects;

FIG. 8 is a table of pharmacokinetic parameters for LSD based on compartmental modeling;

FIG. 10 is a table of characteristics of subjective response;

FIG. 11 is a table of pharmacokinetic parameters for LSD based on non-compartmental analysis;

FIG. 12 is a table of pharmacokinetic parameters for O-H-LSD based on non-compartmental analysis;

FIG. 13 is a table of pharmacodynamics parameter estimates;

FIG. 14 is a table of drug identification after each session and after the study.

DETAILED DESCRIPTION OF THE INVENTION

Figure 1A:
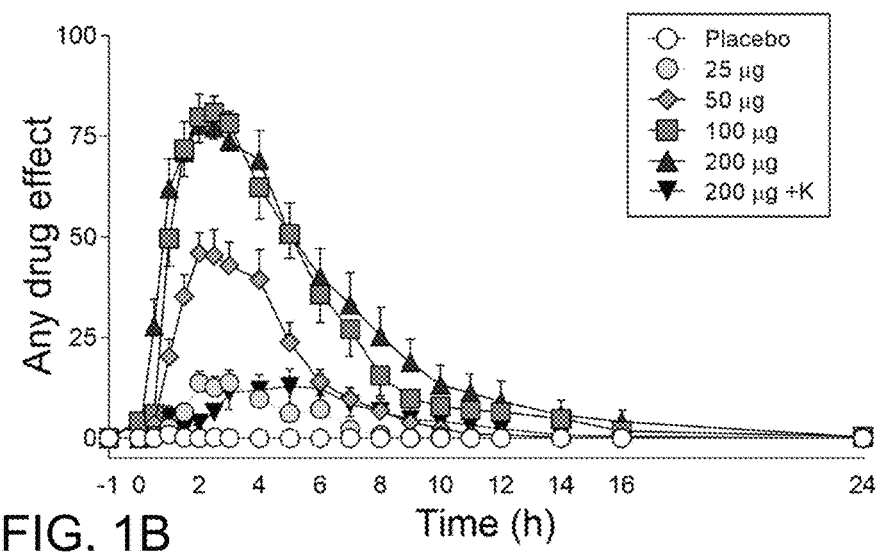
FIG. 1A is a graph of any drug effect versus time.
Figure 1B:
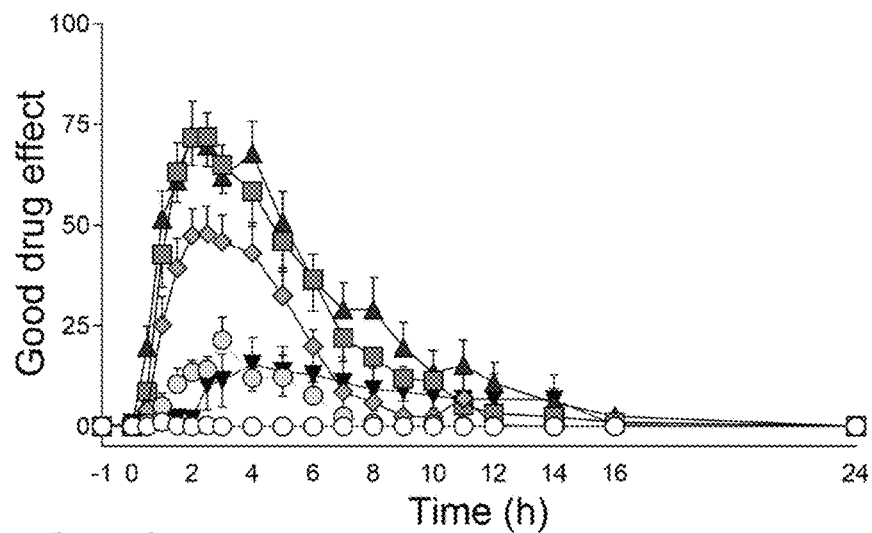
FIG. 1B is a graph of good drug effect versus time.
Figure 1C:
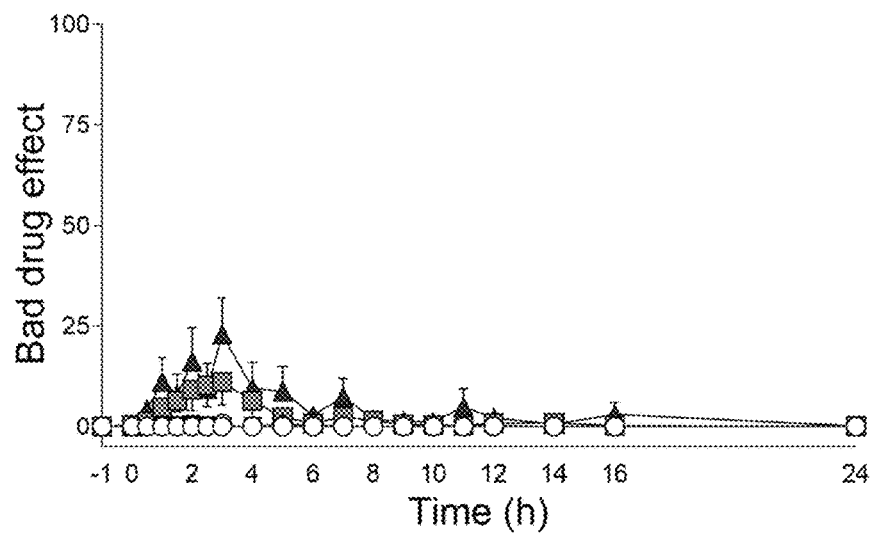
FIG. 1C is a graph of bad drug effect versus time.
Figure 1D:
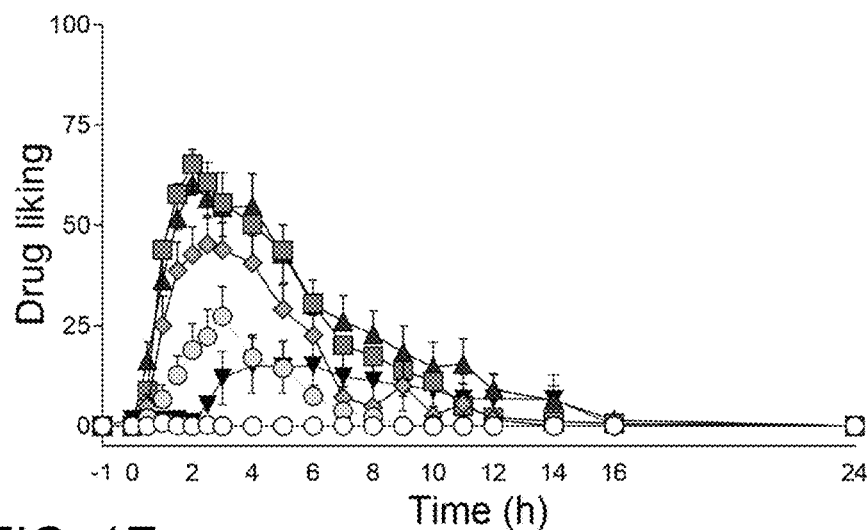
FIG. 1D is a graph of drug liking versus time.
Figure 1E:
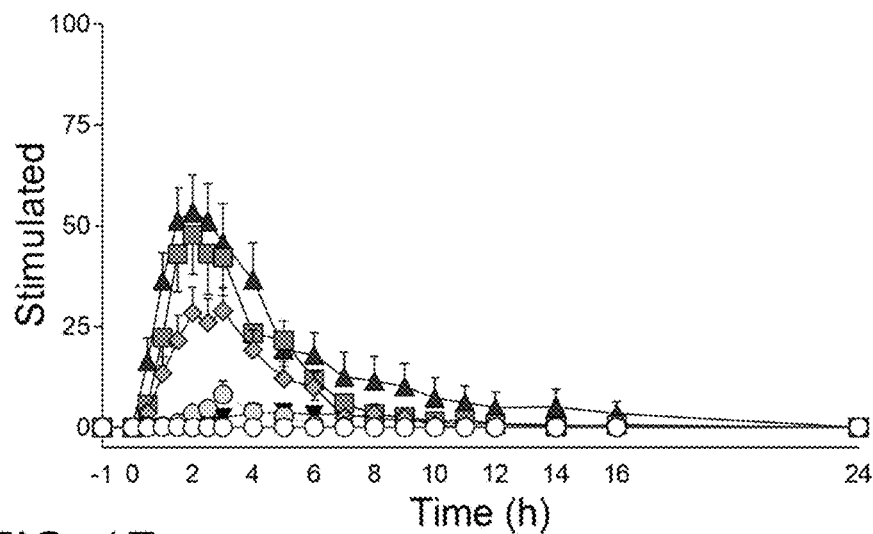
FIG. 1E is a graph of stimulated versus time.
Figure 1F:
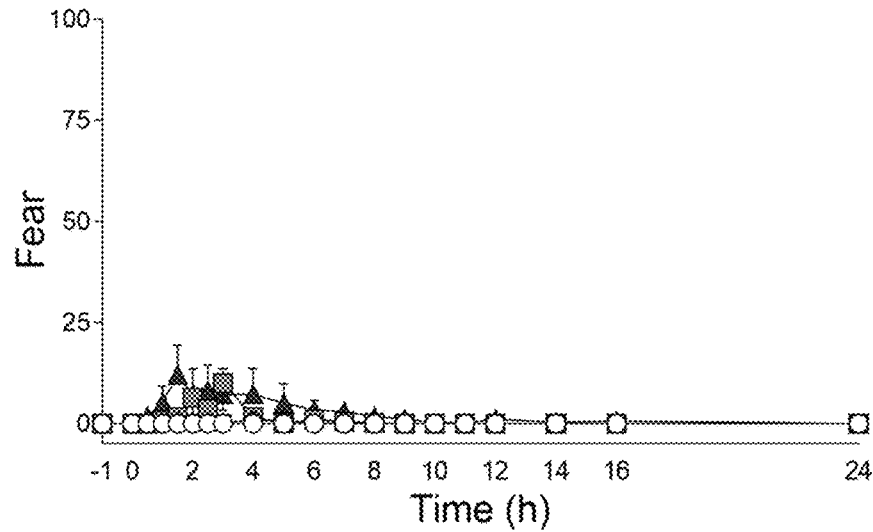
FIG. 1F is a graph of fear versus time.
Figure 1G:
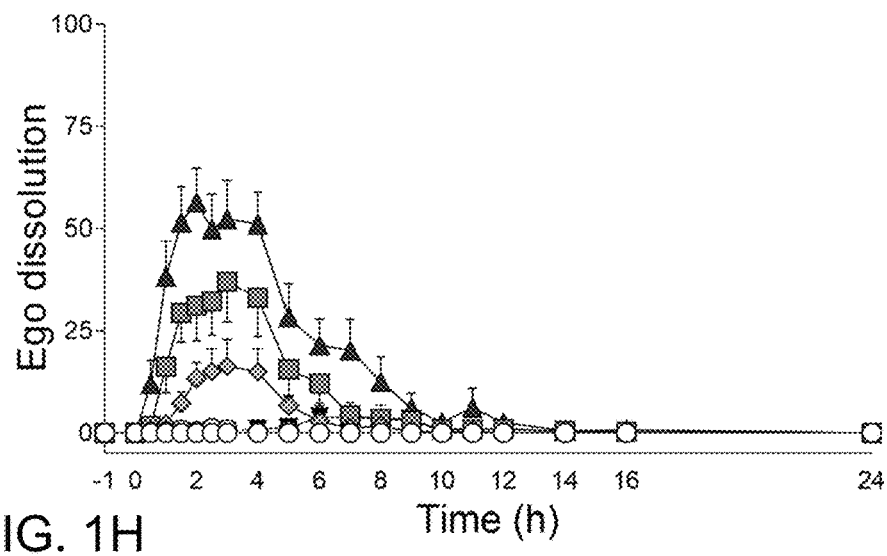
FIG. 1G is a graph of ego dissolution versus time.
Figure 1H:
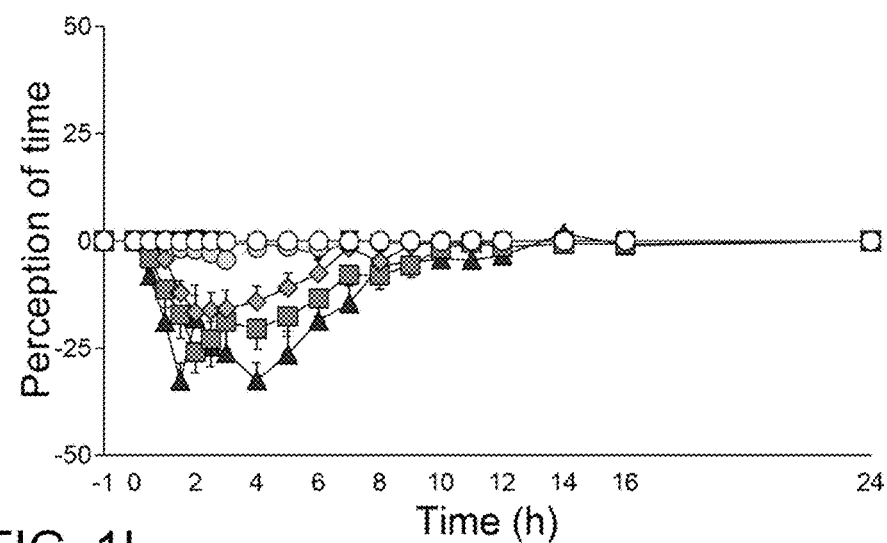
FIG. 1H is a graph of sense of time versus time.
Figure 1I:
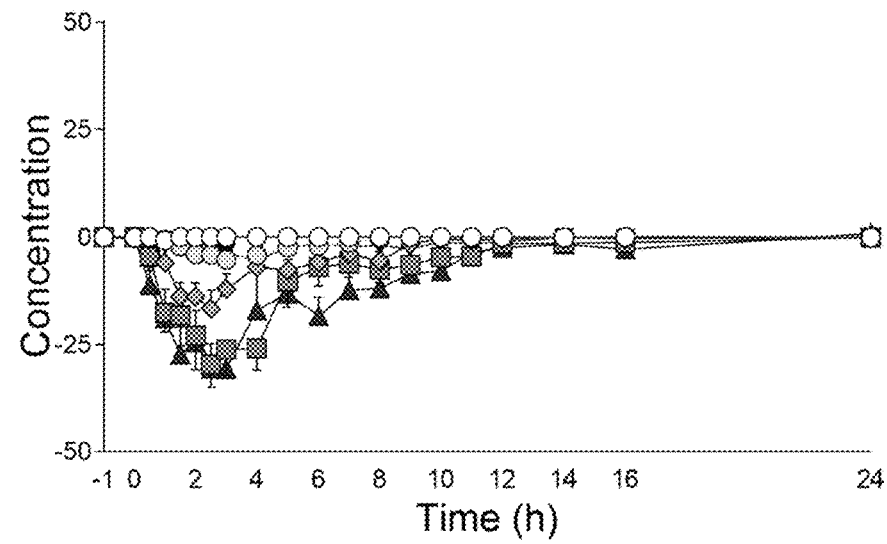
FIG. 1I is a graph of concentration versus time.
Figure 4A:
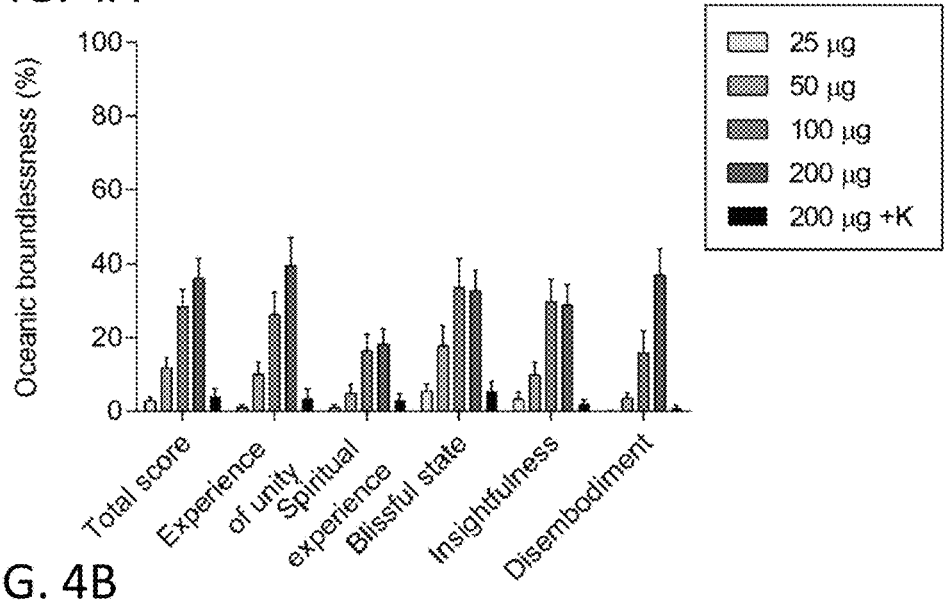
FIG. 4A is a graph of oceanic boundlessness.
Figure 4B:
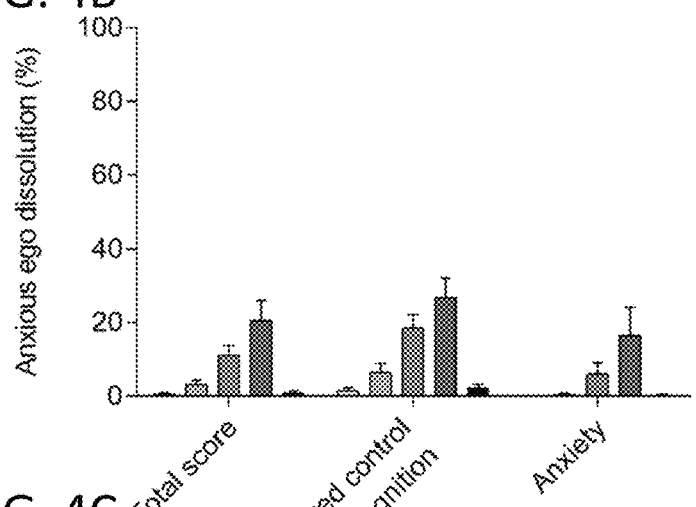
FIG. 4B is a graph of anxious ego dissolution.
Figure 4C:
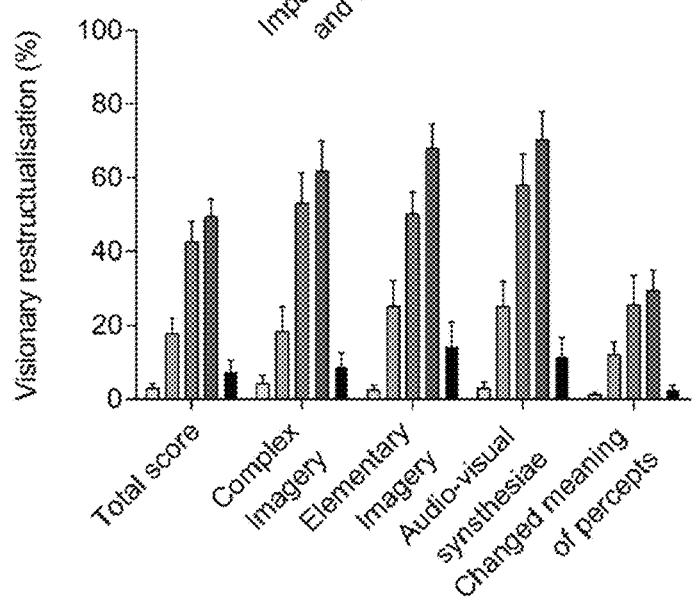
FIG. 4C is a graph of visionary restructuralization.
Figure 5:
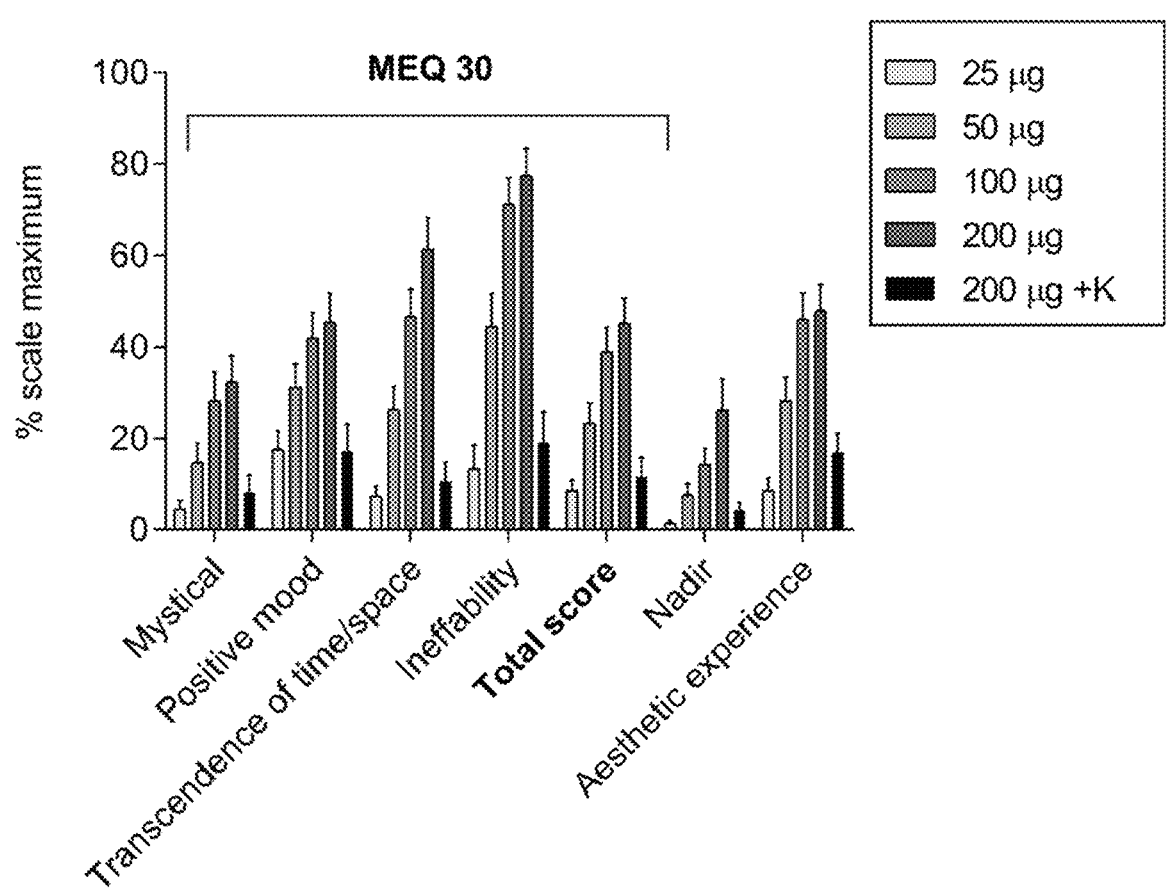
FIG. 5 is a graph of % scale maximum.
Figure 6A:
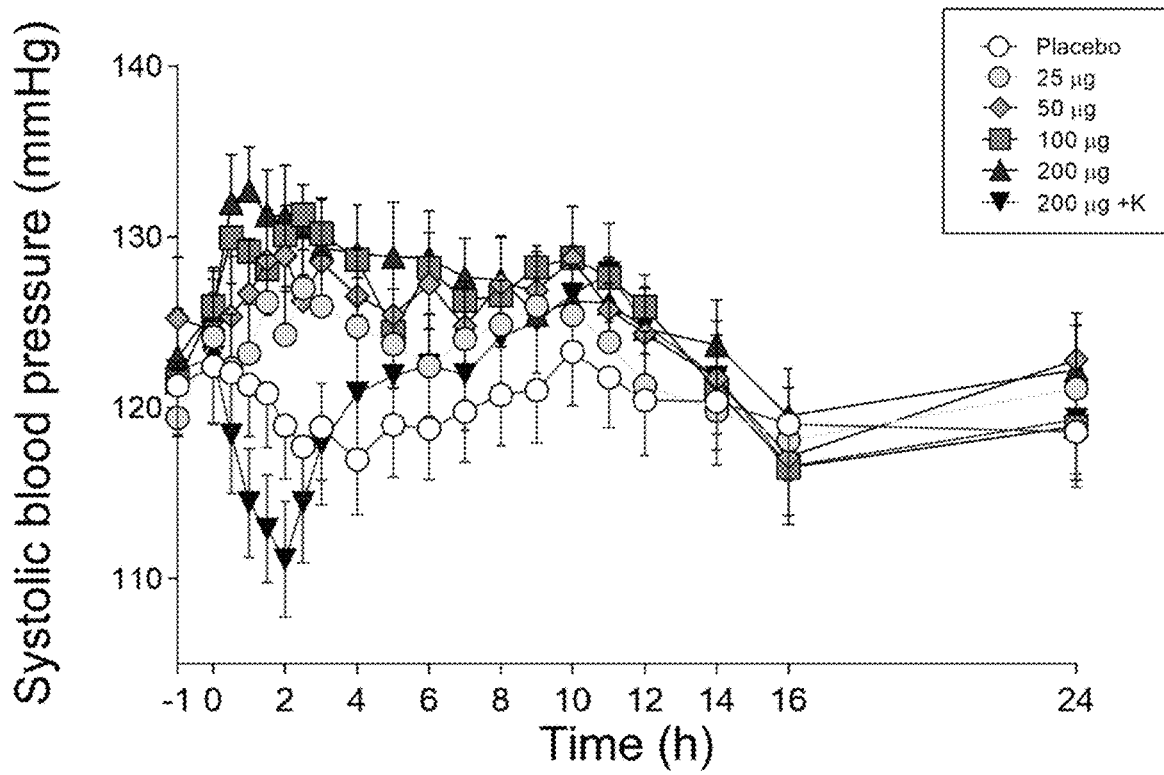
FIG. 6A is a graph of systolic blood pressure versus time.
Figure 6B:
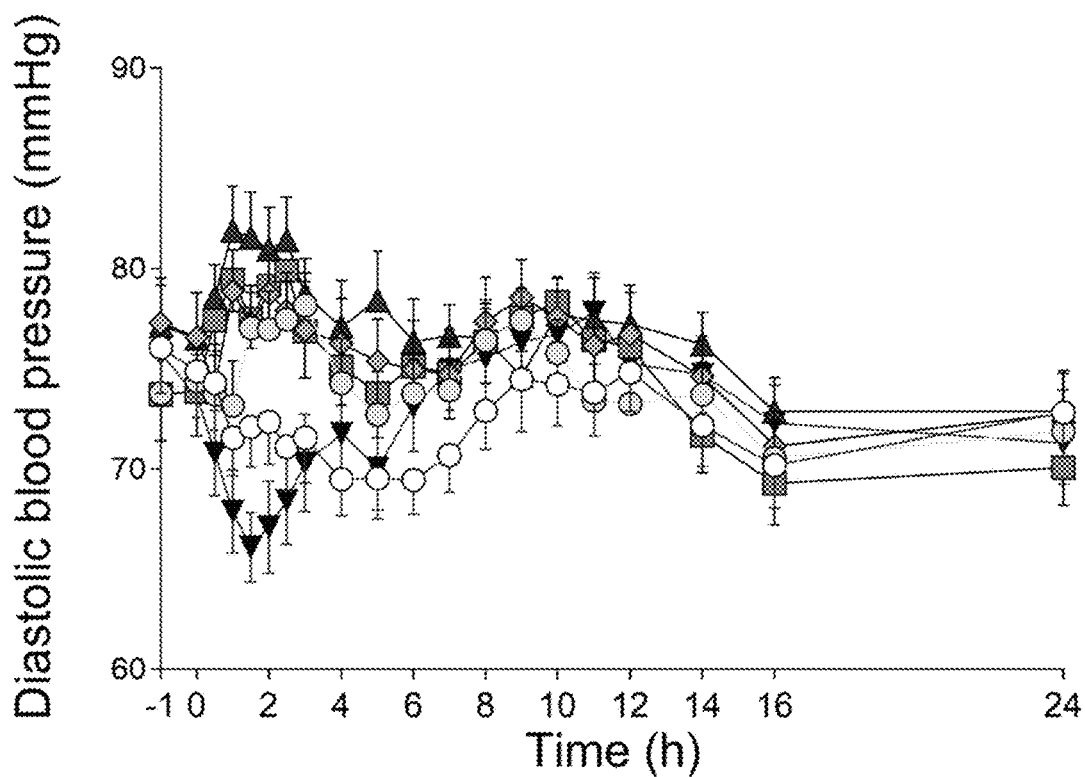
FIG. 6B is a graph of diastolic blood pressure versus time.
Figure 6C:
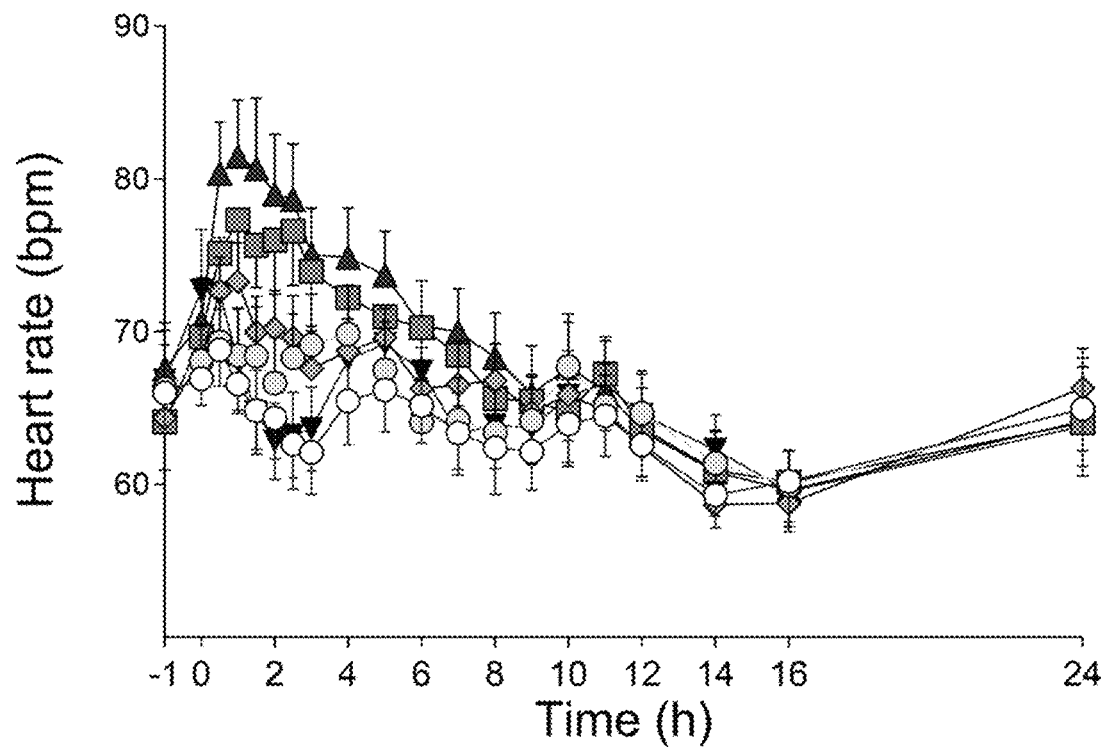
FIG. 6C is a graph of heart rate versus time.
Figure 6D:
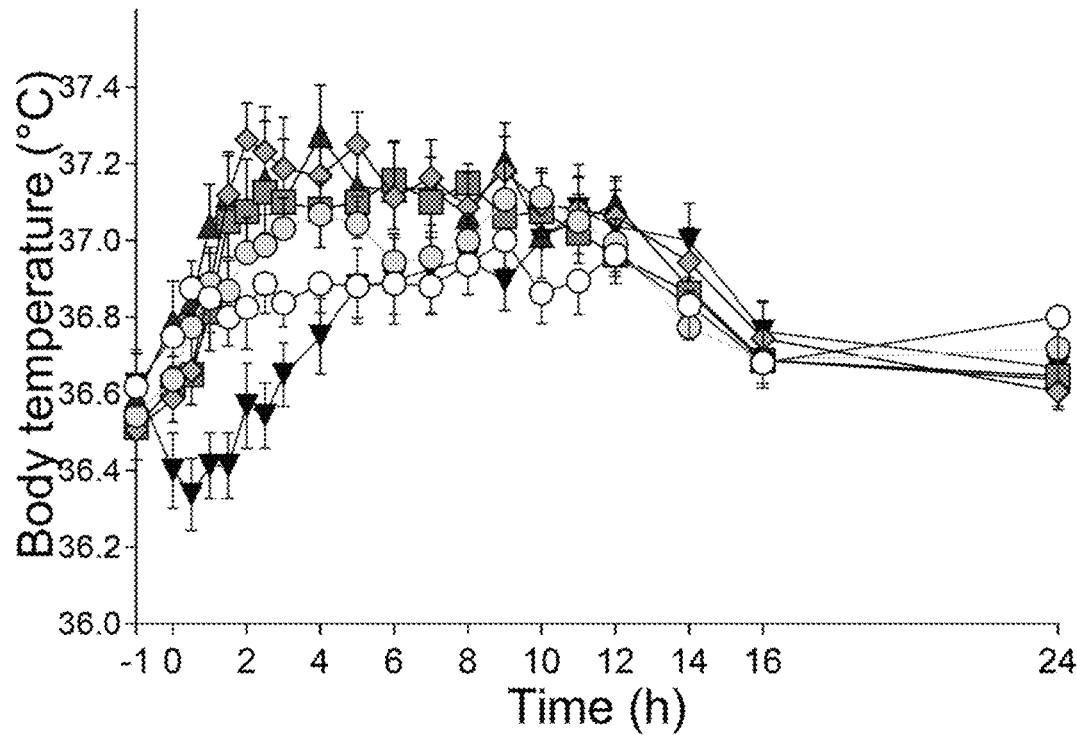
FIG. 6D is a graph of body temperature versus time.

The present invention relates to the use of specific doses of psychedelics such as LSD (lysergic acid diethylamide) to produce defined subjective drug effects in helping to treat medical conditions. An oral LSD solution with documented long-term stability (single dose units) and high content uniformity was used to generate the data underlying the present invention.

LSD can be used to assist psychotherapy, typically at acutely psychoactive doses, for many indications including anxiety, depression, addiction, personality disorder, and others and can also be used to treat other disorders such as cluster headache, migraine, and others (Hintzen & Passie, 2010; Liechti, 2017; Nichols, 2016; Passie et al., 2008). The acute subjective effects of LSD are mostly positive in most humans (Carhart-Harris et al., 2016a; Dolder et al., 2016; Dolder et al., 2017; Holze et al., 2019; Schmid et al., 2015). However, there are also negative subjective effects (anxiety) of LSD in many humans likely depending on the dose of LSD used, personality traits (set) of the person using LSD, the setting (environment) and other factors. The risk of acute negative psychological effects is the main problem of use of psychedelic substances in humans. Anxiety when occurring in LSD-assisted psychotherapy may become a significant problem for both the patient and treating physician. In addition to being highly distressing to the patient, acute anxiety has been linked to a non-favorable long-term outcome in patients with depression (Roseman et al., 2017). Furthermore, anxiety reactions during psychedelic-assisted therapy may require additional supervision, greater engagement of therapists, prolonged sessions, and acute psychological and also pharmacological interventions. Thus, the primary safety concerns relate to psychological rather than somatic adverse effects (Nichols, 2016; Nichols & Grob, 2018). The induction of an overall positive acute response to the psychedelic is critical because several studies showed that a more positive experience is predictive of a greater therapeutic long-term effect of the psychedelic (Garcia-Romeu et al., 2015; Griffiths et al., 2016; Ross et al., 2016). Even in healthy subjects, positive acute responses to psychedelics including LSD have been shown to be linked to more positive long-term effects on well-being (Griffiths et al., 2008; Schmid & Liechti, 2018).

Moderate anticipatory anxiety is common at the beginning of the onset of a drug's effects (Studerus et al., 2012). In a study in sixteen healthy humans, after administration of 0.2 mg of LSD, marked anxiety was observed in two subjects. This anxiety was related to fear of loss of thought control, disembodiment and loss of self (Schmid et al., 2015) and similarly described for psilocybin (Hasler et al., 2004). Bad drug effects (50% or more on a 0-100% scale at any time point after drug administration) were noted in 9 of 16 subjects (56%) after a high dose of 0.2 mg of LSD and in 3 of 24 subjects (12.5%) after a moderate 0.1 mg dose of LSD (Dolder et al., 2017). Similarly, another study reported transient bad drug effects in 7 of 24 subjects (29%) after administration of 0.1 mg of LSD (Holze et al., 2019). Although, these negative subjective drug effects were transient and occurred in subjects who all reported also good drug effects at other or similar time points, negative responses are an issue. One solution to address negative drug effects is to reduce the dose of the psychedelic but this would also reduce at least in part the desired drug effects. Another possibility is that a high dose can be spread out over several days/weeks by giving smaller doses over a longer time period.

The present invention can be used to avoid states of acute anxiety when using psychedelics in a psychiatric or other medical setting and the present invention specifically allows the identification of doses less likely to induce anxiety while still producing the desired good drug effects.

Generally, the present invention provides for a method of dosing and treating patients with a psychedelic, by administering a psychedelic (such as LSD or a salt thereof) at a specific dose defined below such as a microdose, minidose, psychedelic dose, good effect dose, ego-dissolution dose, or cardiovascular safe dose, and producing maximum positive subjective acute effects that are known to be associated with more positive long-term outcomes and minimizing negative acute effects. Defined doses of the psychedelic can be administered with specific acute effects defined for a dose and specific indications for defined doses of the psychedelic. The overall goal of the present invention is to improve the positive over negative acute subjective effect response to a psychedelic. With this goal the method can be used for any indication of psychedelic medication and typically applies to indications where a positive experience after psychedelic use predicts the long-term effects such as in psychiatric disorders including (but no limited to) depression, anxiety, and addiction.

"Positive acute effects" as used herein refers primarily to an increase in subjective rating of "good drug effect" and may also include ratings of "drug liking", "well-being", "oceanic boundlessness", "experience of unity", "spiritual experience", "blissful state", "insightfulness", any "mystical-type experience" and positively experienced "psychedelic effects", and "aspects of ego-dissolution" if experienced without anxiety.

"Negative acute effects" as used herein refers primarily to subjective ratings of "bad drug effect" and "anxiety" and "fear" and may additionally include increased ratings of "anxious ego-dissolution", or descriptions of acute paranoia or states of panic an anxiety as observed by others.

The dose can be effective as inducing an acute psychedelic state. With LSD, the dose can be sufficiently high to produce positive effects (>25 μg LSD base) but also optimized to improve the positive over negative subjective effects profile of LSD (<200 μg base). Plasma concentrations of LSD increase proportionally with increasing doses. LSD produces a dose-depend subjective response starting at the 25 μg dose which produces significant "any drug effects" compared with placebo.

To induce a positive drug effect, doses of LSD are 25-100 μg. Doses <25 μg are too small to produce meaningful acute positive drug effects. A ceiling effect is reached with increasing doses of LSD regarding its positive subjective effects at the 100 μg dose with no significant differences regarding good drug effects between the 100 and 200 μg LSD doses. Thus, doses >100 μg are too high if mainly good subjective drug effects are to be induced. Good drug effects do not increase with doses greater than 100 μg. Only ego-dissolution and anxiety increase with a dose greater than 100 μg of LSD. The time to onset of the LSD response decreases and the time to offset increases resulting in longer effect durations with increasing doses of LSD.

A 200 μg dose of LSD produces significantly greater ego-dissolution and greater anxious ego-dissolution than the 100 μg dose. The 200 μg dose (but not the 100 μg dose) of LSD induces significant anxiety. Thus, doses greater than 100-150 μg are useful if the aim is to induce the experience of ego-dissolution but such experiences are only produced at doses that are also associated with more anxiety compared to lower dose. Doses of 100 μg to 200 μg are subjectively identified as high doses but cannot be distinguished with certainty from each other. Doses of 100 and 200 μg LSD induce similar adverse effects in addition to anxiety.

The following more specific dose ranges can be used in the methods of the present invention.

A "microdose" is a dose of a psychedelic not producing distinct acute subjective drug effects compared with placebo and in line with (Kuypers et al., 2019). A microdose of LSD is 1-20 μg. Such doses have no subjective acute effects but may have therapeutic effects in humans.

A "minidose" is a dose of 21-29 μg of LSD or other psychedelic. A minidose of LSD represents the minimal dose distinguished subjectively by the acute subjective drug effect against placebo and identified correctly as a dose of 25 μg in an experimental study or mistaken as a slightly higher dose of 50 μg LSD.

A "psychedelic dose" is a dose greater than 30 μg of LSD or other psychedelic.

A "good effect dose" is a dose of 30-100 μg of LSD or other psychedelic.

An "ego-dissolution dose" is a dose greater than 100 μg of LSD or other psychedelic. Almost all good and bad effects are the same at doses of 100 μg and 200 μg, except for increases in ego-dissolution and anxiety with the higher dose. If ego-dissolution is not a desired outcome, then using 100 μg would in many cases be the better dose since one can get the same good effects at the lower dose of 100 μg, without the bad effect of increased anxiety. But if one needs ego-dissolution to treat a disease (as further described below), then the 200 μg dose is needed even though anxiety is increased.

A "cardiovascular safe dose" is a dose that is only a moderately cardiostimulant dose of 50-200 μg of LSD or other psychedelic. Cardiovascular adverse effects of LSD are absent at doses <50 μg and minimal at doses up to 200 μg. LSD only moderately but significantly increases blood pressure at doses of 50 μg or higher and heart rate at 100 and 200 μg.

The psychedelics used in the methods of the present invention can be, but are not limited to, LSD, psilocybin, mescaline, dimethyltryptamine (DMT), 2,5-dimethoxy-4- iodoamphetamine (DOI), 2,5-dimethoxy-4-bromoamphetamie (DOB), salts thereof, tartrates thereof, analogs thereof, or homologues thereof.

The compounds of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that they can be administered as the compound and can be administered alone or as an active ingredient in combination with pharmaceutically acceptable carriers, diluents, adjuvants, and vehicles. The compounds can be administered orally, transcutaneously, subcutaneously or parenterally including intravenous, intramuscular, and intranasal administration. The patient being treated is a warm-blooded animal and, in particular, mammals including man. The pharmaceutically acceptable carriers, diluents, adjuvants, and vehicles as well as implant carriers generally refer to inert, non-toxic solid or liquid fillers, diluents or encapsulating material not reacting with the active ingredients of the invention.

The doses can be single doses or multiple doses or a continuous dose over a period of several hours.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The present invention also provides for a method of determining a dose of a psychedelic for an individual, by administering a dose of a psychedelic of a microdose, minidose, psychedelic dose, good effect dose, ego-dissolution dose, or cardiovascular safe dose, determining positive acute effects and negative acute effects in the individual, and adjusting the dose to provide more positive acute effects than negative acute effects in the individual. The individual can be healthy, and the method can be used to predict doses for unhealthy individuals. This method can be used to determine long term dosing and dose schedules. For example, a "good drug effect" dose may be selected to be used first followed by a "ego-dissolution" dose later once the subject or patient is used to the effects of the substance. In addition, dose-finding for clinical trials is difficult and time and money consuming. It would be much easier and cost-effective and rapid if a method were available to define the dose to be used in patients already in Phase 1 studies in healthy subjects. Evaluating the acute effects in healthy subjects with a focus on positive acute over negative effects as a documented predictor of long-term outcome in patients can greatly facilitate the dose-finding for future Phase 2 and Phase 3 studies in patient populations. Therefore, this method can be used in predicting and determining doses for clinical trials.

Methods related to specific doses defined above are also provided.

The present invention provides for a method of treating psychiatric conditions in an individual, by administering a microdose of a psychedelic (preferably LSD) to the individual and treating a psychiatric condition. The psychiatric condition can be, but is not limited to, depression, anxiety, dementia, or attention-deficit hyperactivity disorder. The microdose of LSD induces improvement in the condition with prolonged repeated administration of LSD (such as daily, every other day, every $3^{rd}$-$7^{th}$ day) without producing relevant acute psychedelic drug effects.

The present invention provides for a method of therapy, by administering a good effect dose of a psychedelic (preferably LSD) to an individual and inducing positive acute drug effects that are known to be associated with more positive long-term responses in psychiatric patients. The method can be used in treating various medical conditions including depression, anxiety, substance use disorder, other addiction, personality disorder, eating disorder, post-traumatic stress disorder, obsessive compulsive disorder, various pain disorders, migraine, cluster headache, and palliative care.

The present invention also provides for a method of therapy, by administering an ego-dissolution dose of a psychedelic (preferably LSD) to an individual and providing ego-dissolution. This method is appropriate for individuals experienced with lower good effect doses of LSD or other psychedelics and aiming for a more intense and ego-dissolving experience but also ready to risk experiencing greater anxiety when dealing with this state. Ego-dissolution as experience can be therapeutic in some indications namely in individuals with severe pain disorders, with cancer and/or in palliative care with the goal of being free of pain or at least not realizing somatic pain and the presence of the body or feeling out of the body during this experience. Ego-dissolution can also be a therapeutic experience in other disorders including personality disorder (narcissistic personality disorder) or as needed by psychiatric indications.

In the Example below, LSD (D-lysergic acid diethylamide base, high-performance liquid chromatography purity >99%, Lipomed AG, Arlesheim, Switzerland) was administered in a single oral dose. Each dose of LSD was formulated as a solution to be administered orally in 1 ml of 96% ethanol according to GMP (batch BZ17-2; 25 µg and 100 µg vials) and stored free in argon-prefilled vials in the dark at 4° C. The exact analytically confirmed LSD contents (mean±SD) of the 25 µg and 100 µg formulation were 98.65±1.57 µg (n=9) and 25.68±0.57 µg (n=9), respectively, after production. Stability of the formulation for longer than the study period was documented in an identically produced previous batch (batch BZ16). The isomerization of active LSD to inactive iso-LSD occurred to a small degree when the solution was stored at 4° C. and resulted in iso-LSD contents (% of initial LSD content) of 0.1%, 0.1%, 1.3%, 3.2%, and 3.6% after 4, 6, 12, 18, and 24 months, respectively. No other decomposition products were present. Vials that were stored at room temperature had higher iso-LSD contents of 0%, 3.1%, 3.4%, 6.7%, and 9.5% after 2, 4, 6, 12 and 24 months, respectively. The 100 µg LSD dose of that was used in the present study would correspond to a dose of approximately 125 µg of LSD tartrate including crystal water, which is the form of LSD that is more likely to be used when acquired illegally (i.e., in blotter form) for recreational use or was used in other recent studies (Bershad et al., 2019; Yanakieva et al., 2019).

The present invention also includes data on the effects of doses of LSD of 25, 50, 100 and 200 µg administered within the same study and with all doses administered to the same subject allowing for within-subject dose comparisons without adding the large variance of inter-subject comparisons. Thereby it was possible to define doses of LSD producing specific effects in healthy subjects. Importantly, acute effects of LSD in healthy subjects are comparable to those in patients (Liechti et al., 2017) and similar responses in patients and define medical conditions for which such acute responses are desirable can be assumed. Thus, dosing propositions are made based on the present data and innovation. Further, in the past it was not clear at what single doses of LSD subjective effects become apparent. Doses not producing acute subjective effects have typically been referred to as "microdoses" that may not acutely impair cognition but may have lasting effects on mood and cognition (Hutten et al., 2019). However, as for large LSD doses the dose levels for microdoses vs. high psychedelic doses are not defined and the cut-off is unclear and debated (Kuypers et al., 2019). Thus, the present invention also defines microdoses and the cut-off based on the use of defined doses of LSD in the supporting data.

The following conditions were observed in the Example. 1) The invention is based on a specific setting consisting of only one patient present during the administration of LSD and not including a group setting where more than one person is dosed and where the dose-response effects may differ. 2) The persons or patients treated are not in acute psychological distress prior to the dosing of LSD. 3) The persons do not have an increased risk of psychosis (schizophrenia). 4) The persons are not under the acute influence of other psychoactive substances. 5) The doses refer to LSD base doses and an immediate release formulation. 6) LSD salt doses would need to be transformed to LSD base doses (125 µg LSD tartrate corresponds to 100 µg LSD base used as reference here). 7) The person is comfortably resting in a controlled quiet environment protected from loud noise, other persons (besides from 1-3 supervisors/therapists) with the option of playing suitable music and wearing eye shades or closing eyes. Psychedelics can induce neuroregeneration (Ly et al., 2018). Plasma brain-derived neurotrophic factor (BDNF) levels are a possible biomarker for neurogenesis (Haile et al., 2014). Higher BDNF levels were associated with lower depression ratings after administration of ayahuasca (de Almeida et al., 2019).

The present invention also provides for a method of monitoring individuals for a response of their depression after treatment with LSD, by measuring levels of BDNF in the individual before and after LSD treatment, and determining whether the individual responded to LSD treatment if BDNF increased. BDNF is a growth factor found in the brain and periphery and supports survival of existing neurons and promotes growth and differentiation of new neurons and synapses, important for learning and memory. BDNF can also be found in the retina, kidney, saliva, prostate, motor neurons, and skeletal muscle. BDNF binds with TkrB and LNGFR receptors on cell surfaces and can modulate other neurotransmitter receptors. Exposure to stress and the stress hormone corticosterone can decrease expression of BDNF, causing atrophy of the hippocampus, which can lead to depression. Low levels of BDNF in an individual can be associated with higher depression, and higher levels of BDNF can be associated with lower depression and with the response to treatment. EXAMPLE 2 provides further details on BDNF. BDNF can be measured by taking a blood sample from the individual and performing an ELISA or other immune assay. Dosing of LSD can then be adjusted based on the levels of BDNF detected to provide fewer side effects for the individual.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

Example 1

This study was also shown in Holze, et al. (Holze et al., 2021). The following key findings were observed. LSD exhibited dose-dependent subjective responses starting at the 25 µg dose, which produced significant "any drug effects" compared with placebo. A ceiling effect was reached with increasing doses of LSD on most scales (particularly those referring to positive subjective effects) at the 100 µg dose with typically no significant differences between the 100 and 200 µg LSD doses. The 200 µg dose produced significantly greater ego-dissolution on the VAS, greater anxious ego-dissolution on the 5D-ASC, and a greater subjectively negative nadir effects than the 100 µg dose. Only the 200 µg but not the 100 µg dose of LSD induced significant anxiety on the 5D-ASC and AMRS. Thus, only ego-dissolution and anxiety increased with a dose greater than 100 μg of LSD. LSD only moderately but significantly increased blood pressure at doses of 50 μg or higher and heart rate at 100 and 200 μg (FIG. 3, 6A-6C). LSD at doses of 100 and 200 μg increased adverse effects on the LC compared with placebo. Plasma concentrations of LSD increased proportionally with increasing doses, but good drug effects of LSD showed a ceiling effect at 100 μg while higher bad drug effects and greater ego dissolution were reported at 200 μg compared with 100 μg. The time to onset of the LSD response decreased and the time to offset increased resulting in longer effect durations with increasing doses of LSD. Doses of 100 μg to 200 μg were subjectively identified as high doses but could not be distinguished from each other. A dose of 25 μg of LSD was distinguished from placebo and identified correctly or as 50 μg LSD by most participants.

Materials and Methods

Study design: The study used a double-blind, placebo-controlled, cross-over design with six experimental test sessions to investigate the responses to 1) placebo 2) 25 μg, 3) 50 μg, 4) 100 μg, 5) 200 μg LSD, and 6) 200 μg LSD after ketanserin (40 mg). The washout periods between sessions were at least 10 days. The study was registered at Clinical-Trials.gov (NCT03321136).

Participants: Sixteen healthy subjects (eight men and eight women; mean age±SD: 29±6.4 years; range: 25-52 years). Participants who were younger than 25 years old were excluded from participating in the study. Additional exclusion criteria were age >65 years, pregnancy (urine pregnancy test at screening and before each test session), personal or family (first-degree relative) history of major psychiatric disorders (assessed by the Semi-structured Clinical Interview for *Diagnostic and Statistical Manual of Mental Disorders,* 4th edition, Axis I disorders by a trained psychiatrist), the use of medications that can interfere with the study medications (e.g. antidepressants, antipsychotics, sedatives), chronic or acute physical illness (abnormal physical exam, electrocardiogram, or hematological and chemical blood analyses), tobacco smoking (>10 cigarettes/day), lifetime prevalence of illicit drug use >10 times (except for $\Delta^9$-tetrahydrocannabinol), illicit drug use within the last 2 months, and illicit drug use during the study (determined by urine drug tests).

Study Drugs: LSD (D-lysergic acid diethylamide base, high-performance liquid chromatography purity >99%; Lipomed AG, Arlesheim, Switzerland) was administered as oral solution in units containing 100 (Holze et al., 2019) or 25 μg LSD in 1 mL of 96% ethanol. Thus, subjects ingested 2 mL of LSD solution and/or placebo (96% ethanol) per session: 1) placebo/placebo, 2) 25 μg LSD/placebo, 3) 25 μg LSD/25 μg LSD, 4) 100 μg LSD/placebo, 5) 100 μg LSD/100 μg LSD, 6. 100 μg LSD/100 μg LSD). Ketanserin was obtained as the marketed drug (KETENSIN®, Janssen) and encapsulated with opaque capsules to ensure blinding. Placebo consisted of identical opaque capsules filled with mannitol. Thus, blinding to treatment was guaranteed by using a double-dummy method, with identical capsules and vials that were filled with mannitol and ethanol, respectively, as placebo. At the end of each session and at the end of the study, the participants were asked to retrospectively guess their treatment assignment.

Study procedures: The study included a screening, six 25 hour test sessions, and an end-of-study visit. The sessions were conducted in a calm standard hospital room. Only one research subject and one investigator were present during the test sessions. The test sessions began at 7:45 AM. The subjects then underwent baseline measurements. Ketanserin (40 mg) or placebo was administered at 8:00 AM. LSD or placebo was administered at 9:00 AM. The outcome measures were repeatedly assessed for 24 hours. A standardized lunch and dinner were served at 1:30 PM and 6:00 PM, respectively. The subjects were under constant supervision by an investigator until 1:00 AM. Thus, the subjects were never alone during the first 16 hours after drug administration, and the investigator was in a room next to the subject for up to 24 hours. The subjects were sent home the next day at 9:15 AM.

Subjective drug effects: Subjective effects were assessed repeatedly using visual analog scales (VASs) 1 hour before and 0, 0.5, 1, 1.5, 2, 2.5, 3, 4, 5, 6, 7, 8, 9, 10, 11, 12, 14, 16, and 24 hours after LSD administration. The VASs included "any drug effect," "good drug effect," "bad drug effect," "drug liking," "drug high," "stimulated," "fear," "ego dissolution," "perception of time," and "concentration" (Hysek et al., 2014). The VASs were presented as 100-mm horizontal lines (0-100%), marked from "not at all" on the left to "extremely" on the right. The VASs for "concentration", and "perception of time" were bidirectional (±50%). Marked from "not at all" on the left (−50), to "normal" in the middle (0), to "extremely" on the right (+50) for concentration and "slowed" (−50) and "racing" (+50) for "perception of time". The 5D-ASC scale (Dittrich, 1998; Studerus et al., 2010) was administered 24 hours after LSD administration to retrospectively rate alterations in waking consciousness induced by the drugs. Mystical experiences were assessed using the German version (Liechti et al., 2017) of the 100-item States of Consciousness Questionnaire (SOCQ) (Griffiths et al., 2006) that includes the 43-item and newer 30-item MEQ (MEQ43 (Griffiths et al., 2006) and MEQ30 (Barrett et al., 2015)). The 60-item Adjective Mood Rating Scale (AMRS) (Janke & Debus, 1978) was administered 1 hour before and 3, 6, 9, 12, and 24 hours after drug administration.

Autonomic, adverse, and endocrine effects: Blood pressure, heart rate, and tympanic body temperature were repeatedly measured 1 hour before and 0, 0.5, 1, 1.5, 2.5, 3, 4, 5, 6, 7, 8, 9, 10, 11, 12, 14, 16, and 24 hours after drug administration as previously described in detail (Hysek et al., 2010). Adverse effects were systematically assessed 1 hour before and 12 and 24 hours after drug administration using the 66-item List of Complaints (Zerssen, 1976). This scale yields a total adverse effects score and reliably measures physical and general discomfort.

Plasma drug concentrations: Blood was collected into lithium heparin tubes 1 hour before and 0, 0.5, 1, 2, 3, 4, 6, 8, 10, 12, 14, 16, and 24 hours after LSD administration. The blood samples were immediately centrifuged, and the plasma was subsequently stored at −80° C. until analysis. Plasma concentrations of LSD and O-H-LSD were determined using a validated ultra-high-performance liquid chromatography tandem mass spectrometry method as described previously in detail (Holze et al., 2019).

Pharmacokinetic analyses and pharmacokinetic-pharmacodynamic modeling: Pharmacokinetic parameters were estimated using a one-compartment model with first-order input, first-order elimination, and no lag time in Phoenix WinNonlin 6.4 (Certara, Princeton, N.J., USA) as described previously in detail (Holze et al., 2019).

Data analysis: Peak ($E_{max}$ and/or $E_{min}$) or peak change from baseline ($\Delta E_{max}$) values were determined for repeated measures. The values were then analyzed using repeated-measures analysis of variance (ANOVA), with drug as within-subjects factor, followed by Tukey post hoc comparisons using Statistica 12 software (StatSoft, Tulsa, Okla., USA). The criterion for significance was p<0.05.

Results

Subjective drug effects: Subjective effects over time on the VAS and AMRS are shown in FIGS. 1A-1I and FIGS. 2A-2F, respectively. LSD or placebo was administered at t=0 hour. LSD induced dose-dependent good drug effects up to the 100 µg dose. The 200 µg dose of LSD further increased ego dissolution compared with the 100 µg dose, but not the good drug effects or drug liking associate with LSD. The data are expressed as the mean±SEM % maximal values in 16 subjects. The corresponding peak responses and statistics are presented in FIG. 3. Alterations of mind and mystical-type effects are shown in FIGS. 4A-4C and FIG. 5, respectively, and statistics in FIG. 3. Ratings for placebo were not expressed here, because they are too low for visualization. LSD exhibited dose-depend subjective responses starting at the 25 µg dose which produced significant "any drug effects" compared with placebo (P<0.05). A ceiling effect was reached with increasing doses of LSD on most scales (particularly those referring to positive subjective effects) at the 100 µg dose with typically no significant differences between the 100 and 200 µg LSD doses (FIGS. 1A-1I, 4A-4C, and 5). However, the 200 µg dose produced significantly greater ego-dissolution on the VAS (FIGS. 1A-1I), greater anxious ego-dissolution on the 5D-ASC (FIGS. 4A-4C), and a greater subjectively negative nadir effects (FIG. 5) than the 100 µg dose (all P<0.05). Consistently, only the 200 µg but not the 100 µg dose of LSD induced significant anxiety on the 5D-ASC (FIGS. 4A-4C) and AMRS (FIGS. 2A-2F) (P<0.01 for both). Thus, only ego-dissolution and anxiety increased with a dose greater than 100 µg of LSD.

Cardiovascular, autonomic, adverse, and endocrine effects: Autonomic effects over time and the respective peak effects are shown in FIGS. 6A-6D and FIG. 3, respectively. Frequently reported adverse effects are presented in FIG. 7. LSD only moderately but significantly increased blood pressure at doses of 50 µg or higher and heart rate at 100 and 200 µg (FIGS. 6A-6D). LSD had no effect on body temperature. LSD at doses of 100 and 200 µg increased the total acute (0-12 hours) adverse effects score on the LC compared with placebo and all other conditions. No severe adverse events were observed.

Figure 9A:
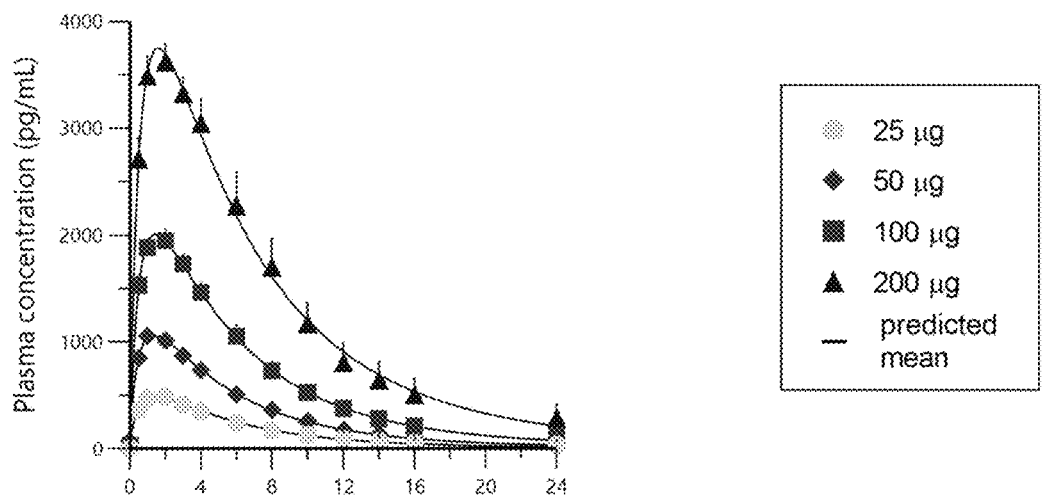
FIG. 9A is a graph of plasma LSD concentration-time curves for 25, 50, 100, and 200 µg.
Figure 9B:
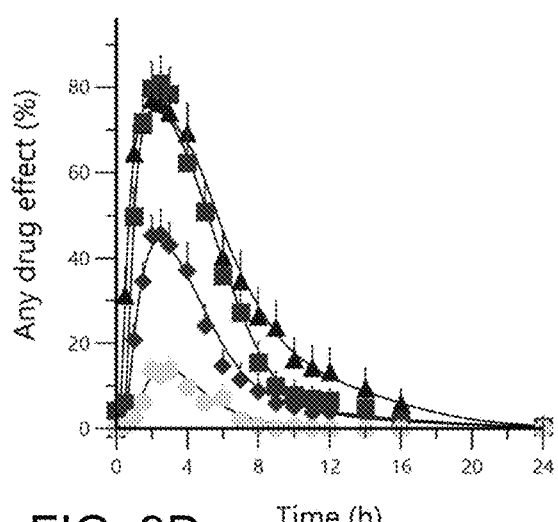
FIGS. 9B-9E show LSD effect-time curves for Visual Analog Scale ratings (0-100%) of (FIG. 9B) "any drug effect," (FIG. 9C) "good drug effect," (FIG. 9D) "bad drug effect," and (FIG. 9E) "ego dissolution"
Figure 9C:
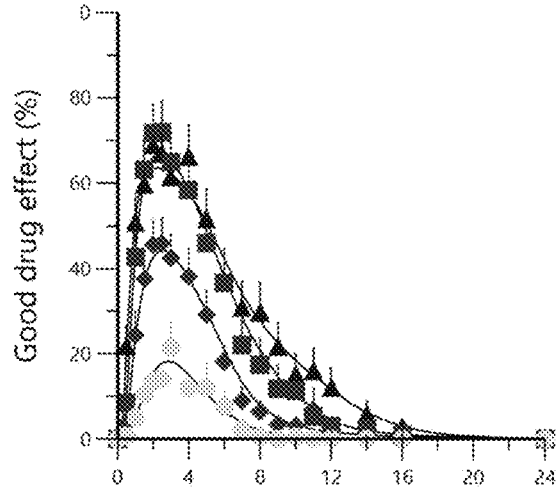
Figure 9D:
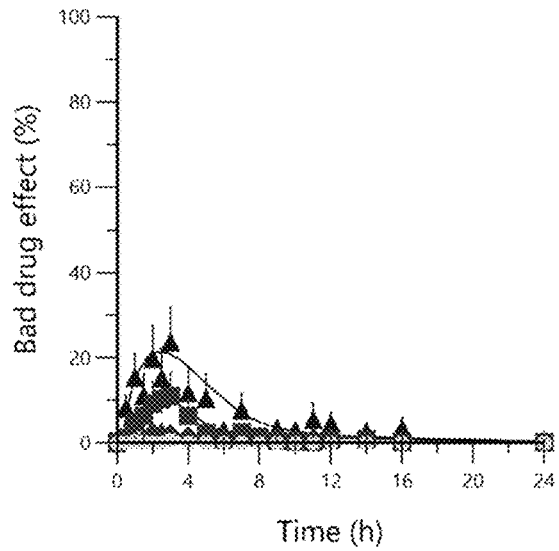
Figure 9E:
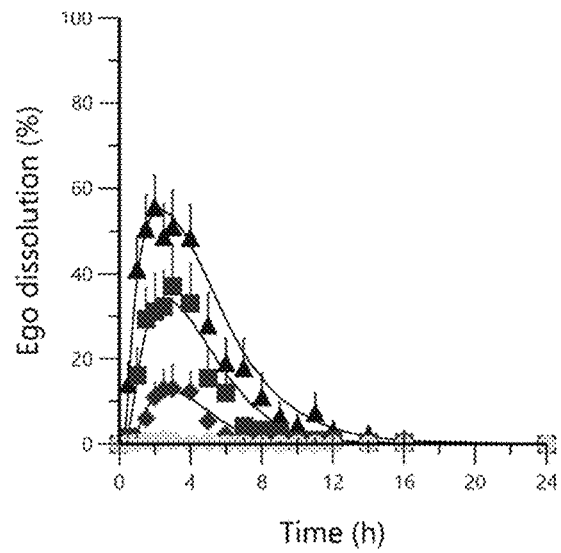

Pharmacokinetics: FIG. 8 shows the pharmacokinetic parameters of LSD. Model-predicted LSD concentrations and effects over time are shown in FIGS. 9A-9E. Plasma concentrations of LSD increased proportionally with increasing doses (FIGS. 9A-9E). FIG. 9A shows plasma LSD concentration-time curves for 25, 50, 100, and 200 µg. FIGS. 9B-9E show LSD effect-time curves for Visual Analog Scale ratings (0-100%) of (FIG. 9B) "any drug effect," (FIG. 9C) "good drug effect," (FIG. 9D) "bad drug effect," and (FIG. 9E) "ego dissolution". While LSD administration resulted in dose-proportional increases in plasma concentrations of LSD, its subjective good drug effects reach a ceiling with no greater positive effects at the 100 compared with the 200 µg dose. In contrast, bad drug effects and ego dissolution increases further with the 200 µg compared with the 100 µg LSD dose indicating that doses higher than 100 µg of LSD produced no greater good drug effects but more ego dissolution and anxiety. The data are expressed as the mean±SEM in 16 subjects after administration of 25, 50, 100, and 200 µg LSD or placebo at t=0 h. The lines represent the mean of the individual predictions based on the pharmacokinetic-pharmacodynamic model. Any and good drug effects of LSD showed a ceiling effect at 100 µg while higher bad drug effects and greater ego dissolution were reported at 200 µg compared with 100 µg (FIGS. 9A-9E). The time to onset of the LSD response decreased and the time to offset increased resulting in longer effect durations with increasing doses of LSD (FIGS. 9A-9E and FIG. 10). Pharmacokinetic parameters based on non-compartmental analyses are shown in FIG. 11 and FIG. 12. Parameters for the PK-PD link model are summarized in FIG. 13.

Blinding: Data on the participants' retrospective identification of the LSD dose condition are shown in FIG. 14. Generally, doses of 100 µg of 200 µg were identified as high doses but could not be distinguished. A dose of 25 µg of LSD was distinguished from placebo and identified correctly or as 50 µg LSD by most participants.

Example 2

Psychedelics can induce neuroregeneration (Ly et al., 2018) and LSD enhances neuronal plasticity. Plasma brain-derived neurotrophic factor (BDNF) levels are a possible biomarker for neurogenesis (Haile et al., 2014). Higher BDNF levels were associated with lower depression ratings after administration of ayahuasca (de Almeida et al., 2019).

Figure 15:
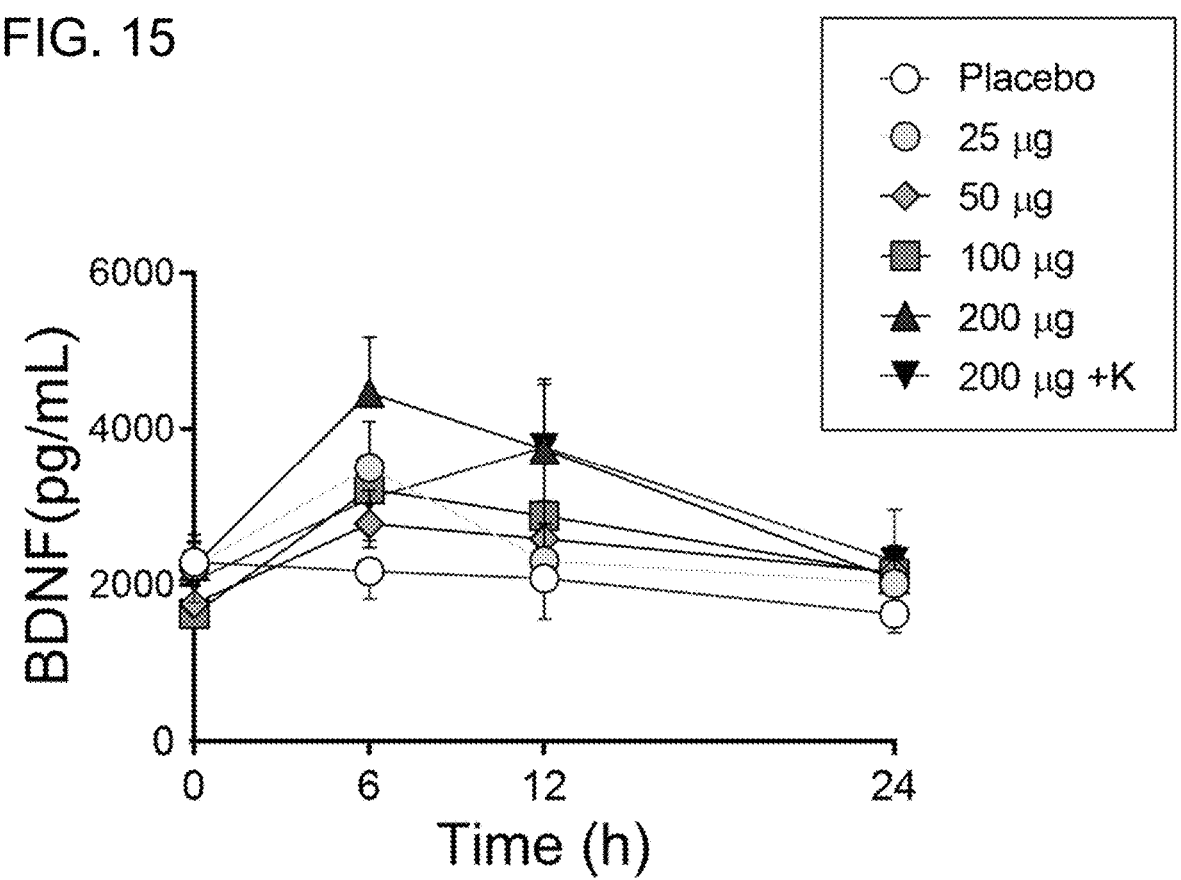
FIG. 15 is a graph of BDNF plasma concentration over time.

Plasma BDNF levels were measured at baseline and 6, 12, and 24 hours after drug administration using the Biosensis Mature BDNF Rapid ELISA Kit (Thebarton, Australia) (Akimoto et al., 2019). FIG. 15 shows that 200 µg LSD significantly increased BDNF plasma concentration compared with placebo with a peak at 6 hours. Additionally, there were non-significant increases in plasma BDNF after lower doses of LSD or after ketanserin with LSD. While BDNF levels are highest with highest LSD dose of 200 µg, lower doses such as 25 µg overlap with higher doses like 100 µg. In other words, lower doses, or microdosing may have as much effect as higher psychedelic doses of 100 µg. Ketanserin blocks LSD side effects at the 5-HT2a receptor when given prior to LSD but BDNF levels go up. BDNF effects are not eliminated by blocking the 5-HT2a receptor which is associated with the psychedelic experience. BDNF can be used as a possible marker for the antidepressant effects of LSD.

Ketanserin can be used together with LSD and blocking the psychedelic response and still allowing for an antidepressant long-term benefit based on the maintained increase of BDNF.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Akimoto H, Oshima S, Sugiyama T, Negishi A, Nemoto T, & Kobayashi D (2019). Changes in brain metabolites 1. related to stress resilience: Metabolomic analysis of the hippocampus in a rat model of depression. Behav Brain Res 359: 342-352.
2. Barrett F S, Johnson M W, & Griffiths R R (2015). Validation of the revised Mystical Experience Questionnaire in experimental sessions with psilocybin. J Psychopharmacol 29: 1182-1190.
3. Barrett F S, Preller K H, Herdener M, Janata P, & Vollenweider F X (2018). Serotonin 2A Receptor Signaling Underlies LSD-induced Alteration of the Neural Response to Dynamic Changes in Music. Cereb Cortex 28: 3939-3950.
4. Bershad A K, Preller K H, Lee R, Keedy S, Wren-Jarvis J, Bremmer M P, & de Wit H (2020). Preliminary report on the effects of a low dose of LSD on resting-state amygdala functional connectivity. Biol Psychiatry Cogn Neurosci Neuroimaging 5: 461-467.
5. Bershad A K, Schepers S T, Bremmer M P, Lee R, & de Wit H (2019). Acute subjective and behavioral effects of microdoses of lysergic acid diethylamide in healthy human volunteers. Biol Psychiatry 86: 792-800.
6. Carhart-Harris R L, Kaelen M, Bolstridge M, Williams T M, Williams L T, Underwood R, Feilding A, & Nutt D J (2016a). The paradoxical psychological effects of lysergic acid diethylamide (LSD). Psychol Med 46: 1379-1390.
7. Carhart-Harris R L, Kaelen M, Whalley M G, Bolstridge M, Feilding A, & Nutt D J (2015). LSD enhances suggestibility in healthy volunteers. Psychopharmacology 232: 785-794.
8. Carhart-Harris R L, Muthukumaraswamy S, Roseman L, Kaelen M, Droog W, Murphy K, Tagliazucchi E, Schenberg E E, Nest T, Orban C, Leech R, Williams L T, Williams T M, Bolstridge M, Sessa B, McGonigle J, Sereno M I, Nichols D, Hellyer P J, Hobden P, Evans J, Singh K D, Wise R G, Curran H V, Feilding A, & Nutt D J (2016b). Neural correlates of the LSD experience revealed by multimodal neuroimaging. Proc Natl Acad Sci USA 113: 4853-4858.
9. de Almeida R N, Galvao A C M, da Silva F S, Silva E, Palhano-Fontes F, Maia-de-Oliveira J P, de Araujo L B, Lobao-Soares B, & Galvao-Coelho N L (2019). Modulation of Serum Brain-Derived Neurotrophic Factor by a Single Dose of Ayahuasca: Observation From a Randomized Controlled Trial. Front Psychol 10: 1234.
10. Dittrich A (1998). The standardized psychometric assessment of altered states of consciousness (ASCs) in humans. Pharmacopsychiatry 31 (Suppl 2): 80-84.
11. Dolder P C, Schmid Y, Mueller F, Borgwardt S, & Liechti M E (2016). LSD acutely impairs fear recognition and enhances emotional empathy and sociality. Neuropsychopharmacology 41: 2638-2646.
12. Dolder P C, Schmid Y, Steuer A E, Kraemer T, Rentsch K M, Hammann F, & Liechti M E (2017). Pharmacokinetics and pharmacodynamics of lysergic acid diethylamide in healthy subjects. Clin Pharmacokinetics 56: 1219-1230.
13. Family N, Maillet E L, Williams L T J, Krediet E, Carhart-Harris R L, Williams T M, Nichols C D, Goble D J, & Raz S (2020). Safety, tolerability, pharmacokinetics, and pharmacodynamics of low dose lysergic acid diethylamide (LSD) in healthy older volunteers. Psychopharmacology 237: 841-853.
14. Garcia-Romeu A, Griffiths R R, & Johnson M W (2015). Psilocybin-occasioned mystical experiences in the treatment of tobacco addiction. Curr Drug Abuse Rev 7: 157-164.
15. Gasser P, Holstein D, Michel Y, Doblin R, Yazar-Klosinski B, Passie T, & Brenneisen R (2014). Safety and efficacy of lysergic acid diethylamide-assisted psychotherapy for anxiety associated with life-threatening diseases. J Nery Ment Dis 202: 513-520.
16. Gasser P, Kirchner K, & Passie T (2015). LSD-assisted psychotherapy for anxiety associated with a life-threatening disease: a qualitative study of acute and sustained subjective effects. J Psychopharmacol 29: 57-68.
17. Griffiths R, Richards W, Johnson M, McCann U, & Jesse R (2008). Mystical-type experiences occasioned by psilocybin mediate the attribution of personal meaning and spiritual significance 14 months later. J Psychopharmacol 22: 621-632.
18. Griffiths R R, Johnson M W, Carducci M A, Umbricht A, Richards W A, Richards B D, Cosimano M P, & Klinedinst M A (2016). Psilocybin produces substantial and sustained decreases in depression and anxiety in patients with life-threatening cancer: a randomized double-blind trial. J Psychopharmacol 30: 1181-1197.
19. Griffiths R R, Richards W A, McCann U, & Jesse R (2006). Psilocybin can occasion mystical-type experiences having substantial and sustained personal meaning and spiritual significance. Psychopharmacology 187: 268-283; discussion 284-292.
20. Haile C N, Murrough J W, Iosifescu D V, Chang L C, Al Jurdi R K, Foulkes A, Iqbal S, Mahoney J J, 3rd, De La Garza R, 2nd, Charney D S, Newton T F, & Mathew S J (2014). Plasma brain derived neurotrophic factor (BDNF) and response to ketamine in treatment-resistant depression. Int J Neuropsychopharmacol 17: 331-336.
21. Hasler F, Grimberg U, Benz M A, Huber T, & Vollenweider F X (2004). Acute psychological and physiological effects of psilocybin in healthy humans: a double-blind, placebo-controlled dose-effect study. Psychopharmacology 172: 145-156.
22. Hintzen A, & Passie T (2010) *The pharmacology of LSD: a critical review*. Oxford University Press: Oxford.
23. Holze F, Duthaler U, Vizeli P, Muller F, Borgwardt S, & Liechti M E (2019). Pharmacokinetics and subjective effects of a novel oral LSD formulation in healthy subjects. Br J Clin Pharmacol 85: 1474-1483.
24. Holze F, Vizeli P, Ley L, Muller F, Dolder P, Stocker M, Duthaler U, Varghese N, Eckert A, Borgwardt S, & Liechti M E (2021). Acute dose-dependent effects of lysergic acid diethylamide in a double-blind placebo-controlled study in healthy subjects. Neuropsychopharmacology 46: 537-544.
25. Hutten N, Mason N L, Dolder P C, & Kuypers K P C (2019). Motives and side-effects of microdosing with psychedelics among users. Int J Neuropsychopharmacol 22: 426-434.
26. Hysek C M, Schmid Y, Simmler L D, Domes G, Heinrichs M, Eisenegger C, Preller K H, Quednow B B, & Liechti M E (2014). MDMA enhances emotional empathy and prosocial behavior. Soc Cogn Affect Neurosci 9: 1645-1652.
27. Hysek C M, Vollenweider F X, & Liechti M E (2010). Effects of a β-blocker on the cardiovascular response to MDMA (ecstasy). Emerg Med J 27: 586-589.
28. Janke W, & Debus G (1978) *Die Eigenschaftswörterliste*. Hogrefe: Göttingen.
29. Kaelen M, Barrett F S, Roseman L, Lorenz R, Family N, Bolstridge M, Curran H V, Feilding A, Nutt D J, & Carhart-Harris R L (2015). LSD enhances the emotional response to music. Psychopharmacology 232: 3607-3614.

30. Kraehenmann R, Pokorny D, Aicher H, Preller K H, Pokorny T, Bosch O G, Seifritz E, & Vollenweider F X (2017a). LSD Increases Primary Process Thinking via Serotonin 2A Receptor Activation. Front Pharmacol 8: 814.
31. Kraehenmann R, Pokorny D, Vollenweider L, Preller K H, Pokorny T, Seifritz E, & Vollenweider F X (2017b). Dreamlike effects of LSD on waking imagery in humans depend on serotonin 2A receptor activation. Psychopharmacology 234: 2031-2046.
32. Krebs T S, & Johansen P O (2013). Over 30 million psychedelic users in the United States. F1000 Res 2: 98.
33. Kuypers K P, Ng L, Erritzoe D, Knudsen G M, Nichols C D, Nichols D E, Pani L, Soula A, & Nutt D (2019). Microdosing psychedelics: more questions than answers? An overview and suggestions for future research. J Psychopharmacol 33: 1039-1057.
34. Liechti M E (2017). Modern clinical research on LSD. Neuropsychopharmacology 42: 2114-2127.
35. Liechti M E, Dolder P C, & Schmid Y (2017). Alterations in conciousness and mystical-type experiences after acute LSD in humans. Psychopharmacology 234: 1499-1510.
36. Ly C, Greb A C, Cameron L P, Wong J M, Barragan E V, Wilson P C, Burbach K F, Soltanzadeh Zarandi S, Sood A, Paddy M R, Duim W C, Dennis M Y, McAllister A K, Ori-McKenney K M, Gray J A, & Olson D E (2018). Psychedelics promote structural and functional neural plasticity. Cell Rep 23: 3170-3182.
37. Mueller F, Dolder P C, Schmidt A, Liechti M E, & Borgwardt S (2018). Altered network hub connectivity after acute LSD administration. Neuroimage Clin 18: 694-701.
38. Mueller F, Lenz C, Dolder P C, Harder S, Schmid Y, Lang U E, Liechti M E, & Borgwardt S (2017a). Acute effects of LSD on amygdala activity during processing of fearful stimuli in healthy subjects. Transl Psychiatry 7: e1084.
39. Mueller F, Lenz C, Dolder P C, Lang U E, Schmidt A, Liechti M E, & Borgwardt S (2017b). Increased thalamic resting-state connectivity as a core driver of LSD-induced hallucinations. Acta Psychiatr Scand 136: 648-657.
40. Nichols D E (2016). Psychedelics. Pharmacological reviews 68: 264-355.
41. Nichols D E, & Grob C S (2018). Is LSD toxic? Forensic science international 284: 141-145.
42. Passie T, Halpern J H, Stichtenoth D O, Emrich H M, & Hintzen A (2008). The pharmacology of lysergic acid diethylamide: a review. CNS Neurosci Ther 14: 295-314.
43. Preller K H, Burt J B, Ji J L, Schleifer C H, Adkinson B D, Stampfli P, Seifritz E, Repovs G, Krystal J H, Murray J D, Vollenweider F X, & Anticevic A (2018). Changes in global and thalamic brain connectivity in LSD-induced altered states of consciousness are attributable to the 5-HT2A receptor. Elife 7: e35082.
44. Preller K H, Herdener M, Pokorny T, Planzer A, Kraehenmann R, Stampfli P, Liechti M E, Seifritz E, & Vollenweider F X (2017). The fabric of meaning and subjective effects in LSD-induced states depend on serotonin 2A receptor activation Curr Biol 27: 451-457.
45. Preller K H, Razi A, Zeidman P, Stampfli P, Friston K J, & Vollenweider F X (2019). Effective connectivity changes in LSD-induced altered states of consciousness in humans. Proc Natl Acad Sci USA 116: 2743-2748.
46. Roseman L, Nutt D J, & Carhart-Harris R L (2017). Quality of acute psychedelic experience predicts therapeutic efficacy of psilocybin for treatment-resistant depression. Front Pharmacol 8: 974.
47. Ross S, Bossis A, Guss J, Agin-Liebes G, Malone T, Cohen B, Mennenga S E, Belser A, Kalliontzi K, Babb J, Su Z, Corby P, & Schmidt B L (2016). Rapid and sustained symptom reduction following psilocybin treatment for anxiety and depression in patients with life-threatening cancer: a randomized controlled trial. J Psychopharmacol 30: 1165-1180.
48. Schmid Y, Enzler F, Gasser P, Grouzmann E, Preller K H, Vollenweider F X, Brenneisen R, Mueller F, Borgwardt S, & Liechti M E (2015). Acute effects of lysergic acid diethylamide in healthy subjects. Biol Psychiatry 78: 544-553.
49. Schmid Y, & Liechti M E (2018). Long-lasting subjective effects of LSD in normal subjects. Psychopharmacology 235: 535-545.
50. Schmidt A, Mueller F, Lenz C, Dolder P C, Schmid Y, Zanchi D, Liechti M E, & Borgwardt S (2017). Acute LSD effects on response inhibition neuronal networks. Psychol Med 48: 1464-1473.
51. Steuer A E, Poetzsch M, Stock L, Eisenbeiss L, Schmid Y, Liechti M E, & Kraemer T (2017). Development and validation of an ultra-fast and sensitive microflow liquid chromatography-tandem mass spectrometry (MFLC-MS/MS) method for quantification of LSD and its metabolites in plasma and application to a controlled LSD administration study in humans. Drug Test Anal 9: 788-797.
52. Studerus E, Gamma A, Kometer M, & Vollenweider F X (2012). Prediction of psilocybin response in healthy volunteers. PLoS One 7: e30800.
53. Studerus E, Gamma A, & Vollenweider F X (2010). Psychometric evaluation of the altered states of consciousness rating scale (OAV). PLoS One 5: e12412.
54. Tagliazucchi E, Roseman L, Kaelen M, Orban C, Muthukumaraswamy S D, Murphy K, Laufs H, Leech R, McGonigle J, Crossley N, Bullmore E, Williams T, Bolstridge M, Feilding A, Nutt D J, & Carhart-Harris R (2016). Increased global functional connectivity correlates with LSD-induced ego dissolution. Curr Biol 26: 1043-1050.
55. Yanakieva S, Polychroni N, Family N, Williams L T J, Luke D P, & Terhune D B (2019). The effects of microdose LSD on time perception: a randomised, double-blind, placebo-controlled trial. Psychopharmacology 236: 1159-1170.
56. Zerssen D V (1976) *Die Beschwerden-Liste. Münchener Informations system*. Psychis: München.

What is claimed is:

1. A method of dosing and treating patients with a psychedelic, including the steps of:
   administering a psychedelic at a dose chosen from the group consisting of a minidose of 21-29 µg, psychedelic dose greater than 30 µg, good effect dose of 30-100 µg, ego-dissolution dose of greater than 100 µg, and cardiovascular safe dose of 50-200 µg, wherein the dose is established through clinical study testing; and
   producing maximum positive subjective acute effects that are known to be associated with more positive long-term outcomes.
2. The method of claim 1, further including the step of minimizing negative acute effects chosen from the group consisting of bad drug effect, anxiety, fear, increased ratings of anxious ego-dissolution, or acute paranoia, states of panic, and combinations thereof.

3. The method of claim 1, wherein the patient is being treated for a condition chosen from the group consisting of depression, anxiety, and addiction.

4. The method of claim 1, wherein the positive subjective acute effects are chosen from the group consisting of good drug effect, drug liking, well-being, oceanic boundlessness, experience of unity, spiritual experience, blissful state, insightfulness, mystical-type experience positively experienced psychedelic effects, aspects of ego-dissolution, and combinations thereof.

5. The method of claim 1, wherein the psychedelic is chosen from the group consisting of LSD, psilocybin, mescaline, dimethyltryptamine (DMT), 2,5-dimethoxy-4-iodo-amphetamine (DOI), 2,5-dimethoxy-4-bromoamphetamie (DOB), salts thereof, tartrates thereof, analogs thereof, and homologues thereof.

6. A method of determining a dose of a psychedelic for an individual, including the steps of:
   administering a dose of a psychedelic to an individual chosen from the group consisting of a minidose of 21-29 µg, psychedelic dose greater than 30 µg, good effect dose of 30-100 µg, ego-dissolution dose of greater than 100 µg, and cardiovascular safe dose of 50-200 µg, wherein the dose is established through clinical study testing;
   determining positive acute effects and negative acute effects in the individual; and
   adjusting the dose to provide more positive acute effects than negative acute effects in the individual.

7. The method of claim 6, wherein the individual is healthy and further including the step of predicting a dose for an unhealthy individual.

8. The method of claim 6, further including the step of determining long term dosing and dose schedules.

9. The method of claim 6, wherein the psychedelic is chosen from the group consisting of LSD, psilocybin, mescaline, dimethyltryptamine (DMT), 2,5-dimethoxy-4-iodo-amphetamine (DOI), 2,5-dimethoxy-4-bromoamphetamie (DOB), salts thereof, tartrates thereof, analogs thereof, and homologues thereof.

10. The method of claim 6, wherein the positive acute effects are chosen from the group consisting of good drug effect, drug liking, well-being, oceanic boundlessness, experience of unity, spiritual experience, blissful state, insightfulness, mystical-type experience positively experienced psychedelic effects, aspects of ego-dissolution, and combinations thereof, and wherein the negative effects are chosen from the group consisting of bad drug effect, anxiety, fear, increased ratings of anxious ego-dissolution, or acute paranoia, states of panic, and combinations thereof.

11. A method of defining therapeutic doses of a psychedelic in clinical trials, including the step of:
   administering a dose of a psychedelic to a healthy individual in a phase 1 study chosen from the group consisting of a minidose, psychedelic dose, good effect dose, ego-dissolution dose, and cardiovascular safe dose, wherein the dose is established through clinical study testing;
   determining positive acute effects and negative acute effects in the individual;
   adjusting the dose to provide more positive acute effects than negative acute effects in the individual; and
   using the adjusted dose for a phase 2 or phase 3 study in patients.

12. The method of claim 11, wherein the psychedelic is chosen from the group consisting of LSD, psilocybin, mescaline, dimethyltryptamine (DMT), 2,5-dimethoxy-4-iodo-amphetamine (DOI), 2,5-dimethoxy-4-bromoamphetamie (DOB), salts thereof, tartrates thereof, analogs thereof, and homologues thereof.

13. The method of claim 11, wherein the positive acute effects are chosen from the group consisting of good drug effect, drug liking, well-being, oceanic boundlessness, experience of unity, spiritual experience, blissful state, insightfulness, mystical-type experience positively experienced psychedelic effects, aspects of ego-dissolution, and combinations thereof, and wherein the negative effects are chosen from the group consisting of bad drug effect, anxiety, fear, increased ratings of anxious ego-dissolution, or acute paranoia, states of panic, and combinations thereof.

14. The method of claim 11, wherein the dose is a microdose of 1-20 µg.

15. The method of claim 11, wherein the dose is a minidose of 21-29 µg.

16. The method of claim 11, wherein the dose is a psychedelic dose of greater than 30 µg.

17. The method of claim 11, wherein the dose is a good effect dose of 30-100 µg.

18. The method of claim 11, wherein the dose is an ego-dissolution dose of greater than 100 µg.

19. The method of claim 11, wherein the dose is a cardiovascular safe dose of 50-200 µg.

20. A method of treating psychiatric conditions in an individual, including the steps of:
   administering a microdose of 1-20 µg of a psychedelic to the individual, wherein the dose is established through clinical study testing; and
   treating a psychiatric condition chosen from the group consisting of anxiety and dementia.

21. The method of claim 20, wherein said administering step is performed at a time chosen from the group consisting of daily, every other day, and every $3^{rd}$-$7^{th}$ day.

22. The method of claim 20, wherein the psychedelic is chosen from the group consisting of LSD, psilocybin, mescaline, dimethyltryptamine (DMT), 2,5-dimethoxy-4-iodo-amphetamine (DOI), 2,5-dimethoxy-4-bromoamphetamie (DOB), salts thereof, tartrates thereof, analogs thereof, and homologues thereof.

23. A method of therapy, including the steps of:
   administering a good effect dose of 30-100 µg of a composition chosen from the group consisting of LSD, salts thereof, tartrates thereof, analogs thereof, and homologues thereof to an individual, wherein the dose is established through clinical study testing, and
   inducing positive acute drug effects that are known to be associated with more positive long-term responses in psychiatric patients.

24. The method of claim 23, wherein the individual has a condition chosen from the group consisting of depression, anxiety, substance use disorder, addiction, personality disorder, eating disorder, post-traumatic stress disorder, obsessive compulsive disorder, pain disorders, migraine, cluster headache, and requiring palliative care.

25. The method of claim 23, wherein the positive acute effects are chosen from the group consisting of good drug effect, drug liking, well-being, oceanic boundlessness, experience of unity, spiritual experience, blissful state, insightfulness, mystical-type experience positively experienced psychedelic effects, aspects of ego-dissolution, and combinations thereof.

26. A method of therapy, including the steps of:
   administering a defined ego-dissolution dose of greater than 100 µg of a composition chosen from the group consisting of LSD, salts thereof, tartrates thereof, analogs thereof, and homologues thereof to an individual, wherein the dose is established through clinical study testing; and providing ego-dissolution.

27. The method of claim 26, wherein the individual has a condition chosen from the group consisting of severe pain disorders, cancer, requiring palliative care, and personality disorder.

28. The method of claim 26, wherein said providing ego-dissolution step further includes a step chosen from the group consisting of allowing the individual to be free of pain, allowing the individual to not realize somatic pain and the presence of their body, and allowing the individual to feel out of their body.

29. A method of monitoring individuals for depression after treatment with LSD, including the steps of:

measuring levels of brain-derived neurotrophic factor (BDNF) in the individual before and after LSD treatment; and determining whether the individual responded to LSD treatment if BDNF increased.

30. The method of claim 29, wherein said measuring step further includes the step of taking a blood sample from the individual and performing an immune assay for BDNF.

31. The method of claim 29, further including the step of adjusting a dose of LSD based on the level of BDNF measured.

* * * * *